(12) United States Patent
Pless et al.

(10) Patent No.: US 7,813,793 B2
(45) Date of Patent: *Oct. 12, 2010

(54) SEIZURE SENSING AND DETECTION USING AN IMPLANTABLE DEVICE

(75) Inventors: Benjamin D. Pless, Atherton, CA (US); Stephen T. Archer, Sunnyvale, CA (US); Craig M. Baysinger, Livermore, CA (US); Barbara Gibb, Foster City, CA (US); Suresh Gurunathan, Palo Alto, CA (US); Bruce Kirkpatrick, Mountain View, CA (US); Thomas K. Tcheng, Pleasant Hill, CA (US)

(73) Assignee: NeuroPace, Inc., Mountain View, CA (US)

( * ) Notice: Subject to any disclaimer, the term of this patent is extended or adjusted under 35 U.S.C. 154(b) by 1205 days.

This patent is subject to a terminal disclaimer.

(21) Appl. No.: 10/973,091

(22) Filed: Oct. 25, 2004

(65) Prior Publication Data

US 2007/0016094 A1    Jan. 18, 2007

Related U.S. Application Data

(63) Continuation of application No. 09/896,092, filed on Jun. 28, 2001, now Pat. No. 6,810,285.

(51) Int. Cl.
*A61B 5/00* (2006.01)
(52) U.S. Cl. .................................................. 600/544
(58) Field of Classification Search .................. None
See application file for complete search history.

(56) References Cited

U.S. PATENT DOCUMENTS

| | | | |
|---|---|---|---|
| 5,215,086 A | 6/1993 | Terry et al. | |
| 5,269,891 A * | 12/1993 | Colin | ....................... 205/777.5 |
| 5,311,876 A | 5/1994 | Olsen et al. | |
| 5,857,978 A | 1/1999 | Hively et al. | |
| 5,938,689 A | 8/1999 | Fischell et al. | |
| 5,995,868 A | 11/1999 | Dorfmesier et al. | |
| 6,006,124 A | 12/1999 | Fischell et al. | |
| 6,016,449 A | 1/2000 | Fischell et al. | |
| 6,018,682 A | 1/2000 | Rise | |
| 6,061,593 A | 5/2000 | Fischell et al. | |
| 6,128,538 A | 10/2000 | Fischell et al. | |
| 6,134,474 A | 10/2000 | Fischell et al. | |
| 6,161,045 A | 12/2000 | Fischell et al. | |
| 6,230,049 B1 | 5/2001 | Fischell et al. | |

(Continued)

OTHER PUBLICATIONS

Gotman, J., Automatic Seizure Detection: Improvements and Evaluation, Electroencephalogr. Clin. Neurophysiol. (1990) 76(4): 317-24.

(Continued)

*Primary Examiner*—Robert L Nasser

(57) ABSTRACT

A system and method for detecting and predicting neurological events with an implantable device uses a relatively low-power central processing unit in connection with signal processing circuitry to identify features (including half waves) and calculate window-based characteristics (including line lengths and areas under the curve of the waveform) in an electrographic signal received from a patient's brain. The features and window-based characteristics are combinable in various ways according to the invention to detect and predict neurological events in real time, enabling responsive action by the implantable device.

19 Claims, 22 Drawing Sheets

U.S. PATENT DOCUMENTS

| | | | |
|---|---|---|---|
| 6,353,754 | B1 | 3/2002 | Fischell et al. |
| 6,354,299 | B1 | 3/2002 | Fischell et al. |
| 6,360,122 | B1 | 3/2002 | Fischell et al. |
| 6,366,813 | B1 * | 4/2002 | DiLorenzo .................. 607/45 |
| 6,427,086 | B1 | 7/2002 | Fischell et al. |
| 6,466,822 | B1 | 10/2002 | Pless |
| 6,473,639 | B1 * | 10/2002 | Fischell et al. .............. 600/544 |
| 6,480,743 | B1 | 11/2002 | Kirkpatrick et al. |
| 6,597,954 | B1 | 7/2003 | Pless et al. |
| 6,810,285 | B2 * | 10/2004 | Pless et al. ................. 600/544 |
| 6,944,501 | B1 | 9/2005 | Pless |
| 7,089,059 | B1 | 8/2006 | Pless |
| 7,146,218 | B2 * | 12/2006 | Esteller et al. ................ 607/45 |

OTHER PUBLICATIONS

Wagner, H. R., et al., Suppression of Cortical Epileptiform Activity By Generalized and Localized ECoG Desynchronization, Electroencephalogr. Clin. Neurophysiol. (1975) 39(5): 499-506.

H. Qu and J. Gotman, A Patient-Specific Algorithm for the Detection of Seizure Onset in Long-Term EEG Monitoring: Possible Use as a Warning Device, IEEE Trans. Biomed. Eng. (1997); 44(2): 115-22.

H. Qu and J. Gotman, A seizure warning system for long term epilepsy monitoring, Neurology 1995; 45: 2250-4.

R. Esteller et al. "Line length: an efficient feature for seizure onset detection" Proceedings of the 23rd. Annual International Conference of the IEEE Engineering in Medicine and Biology Society. 2001 Conference Proceedings. (EMBS). Instanbul, Turkey, Oct. 25-28, 2001; [Annual International Conference of the IEEE Engineering in Medicine and Biology Society. EMBS], vol. 1., p. 1707-1710, XP010594759.

C. Castellaro et al. "Improvements in Automatic Detection of Events in Long Term EEG and Polygraphy" Bollettino—Lega Italiana Contro L'Epilessia, May 13, 1993 Milan, IT vol: 84, pp. 291-301, XP008014892.

Activa Therapy Overview, http://www.medtronic.com/physicianlactiva/index.html, Jun. 5, 2007.

Tarver, T. et al., "An Implantable Neurocybernetic Prosthesis System," http://www.ncbi.nlm.nih.gov, Jun. 12, 2007.

PCT Application PCT/US02/20630, International Search Report Mailed Jun. 5, 2003.

Article 96(2) Communication dated Jun. 4, 2004 for counterpart foreign application EP Patent Application No. 02748010.2-1526.

Applicant Response dated Mar. 16, 2005 to Article 96(2) Communication dated Jun. 4, 2004 for counterpart foreign application EP Patent Application No. 02748010.2-1526.

Article 96(2) Communication dated Oct. 2, 2006 for counterpart foreign application EP Patent Application No. 02748010.2-1526.

Applicant Response dated Apr. 26, 2007 to Article 96(2) Communication dated Oct. 2, 2006 for counterpart foreign application EP Patent Application No. 02748010.2-1526.

Summons to attend oral proceedings dated Jul. 30, 2008 for counterpart foreign application EP Patent Application No. 02748010.2-1526.

* cited by examiner

SEIZURE SENSING AND DETECTION USING AN IMPLANTABLE DEVICE

CROSS-REFERENCE TO RELATED APPLICATION

This is a continuation of U.S. patent application Ser. No. 09/896,092, filed on Jun. 28, 2001 and issued on Oct. 26, 2004 as U.S. Pat. No. 6,810,285.

FIELD OF THE INVENTION

The invention relates to systems and methods for detecting and predicting neurological dysfunction characterized by abnormal electrographic patterns, and more particularly to a system and method for detecting and predicting epileptic seizures and their onsets by analyzing electroencephalogram and electrocorticogram signals with an implantable device.

BACKGROUND OF THE INVENTION

Epilepsy, a neurological disorder characterized by the occurrence of seizures (specifically episodic impairment or loss of consciousness, abnormal motor phenomena, psychic or sensory disturbances, or the perturbation of the autonomic nervous system), is debilitating to a great number of people. It is believed that as many as two to four million Americans may suffer from various forms of epilepsy. Research has found that its prevalence may be even greater worldwide, particularly in less economically developed nations, suggesting that the worldwide figure for epilepsy sufferers may be in excess of one hundred million.

Because epilepsy is characterized by seizures, its sufferers are frequently limited in the kinds of activities they may participate in. Epilepsy can prevent people from driving, working, or otherwise participating in much of what society has to offer. Some epilepsy sufferers have serious seizures so frequently that they are effectively incapacitated.

Furthermore, epilepsy is often progressive and can be associated with degenerative disorders and conditions. Over time, epileptic seizures often become more frequent and more serious, and in particularly severe cases, are likely to lead to deterioration of other brain functions (including cognitive function) as well as physical impairments.

The current state of the art in treating neurological disorders, particularly epilepsy, typically involves drug therapy and surgery. The first approach is usually drug therapy.

A number of drugs are approved and available for treating epilepsy, such as sodium valproate, phenobarbital/primidone, ethosuximide, gabapentin, phenyloin, and carbamazepine, as well as a number of others. Unfortunately, those drugs typically have serious side effects, especially toxicity, and it is extremely important in most cases to maintain a precise therapeutic serum level to avoid breakthrough seizures (if the dosage is too low) or toxic effects (if the dosage is too high). The need for patient discipline is high, especially when a patient's drug regimen causes unpleasant side effects the patient may wish to avoid.

Moreover, while many patients respond well to drug therapy alone, a significant number (at least 20-30%) do not. For those patients, surgery is presently the best-established and most viable alternative course of treatment.

Currently practiced surgical approaches include radical surgical resection such as hemispherectomy, corticectomy, lobectomy and partial lobectomy, and less-radical lesionectomy, transection, and stereotactic ablation. Besides being less than fully successful, these surgical approaches generally have a high risk of complications, and can often result in damage to eloquent (i.e., functionally important) brain regions and the consequent long-term impairment of various cognitive and other neurological functions. Furthermore, for a variety of reasons, such surgical treatments are contraindicated in a substantial number of patients. And unfortunately, even after radical brain surgery, many epilepsy patients are still not seizure-free.

Electrical stimulation is an emerging therapy for treating epilepsy. However, currently approved and available electrical stimulation devices apply continuous electrical stimulation to neural tissue surrounding or near implanted electrodes, and do not perform any detection—they are not responsive to relevant neurological conditions.

The NeuroCybemetic Prosthesis (NCP) from Cyberonics, for example, applies continuous electrical stimulation to the patient's vagus nerve. This approach has been found to reduce seizures by about 50% in about 50% of patients. Unfortunately, a much greater reduction in the incidence of seizures is needed to provide clinical benefit. The Activa device from Medtronic is a pectorally implanted continuous deep brain stimulator intended primarily to treat Parkinson's disease. In operation, it supplies a continuous electrical pulse stream to a selected deep brain structure where an electrode has been implanted.

Continuous stimulation of deep brain structures for the treatment of epilepsy has not met with consistent success. To be effective in terminating seizures, it is believed that one effective site where stimulation should be performed is near the focus of the epileptogenic region. The focus is often in the neocortex, where continuous stimulation may cause significant neurological deficit with clinical symptoms including loss of speech, sensory disorders, or involuntary motion. Accordingly, research has been directed toward automatic responsive epilepsy treatment based on a detection of imminent seizure.

A typical epilepsy patient experiences episodic attacks or seizures, which are generally electrographically defined as periods of abnormal neurological activity. As is traditional in the art, such periods shall be referred to herein as "ictal".

Most prior work on the detection and responsive treatment of seizures via electrical stimulation has focused on analysis of electroencephalogram (EEG) and electrocorticogram (ECoG) waveforms. In general, EEG signals represent aggregate neuronal activity potentials detectable via electrodes applied to a patient's scalp. ECoG signals, deep-brain counterparts to EEG signals, are detectable via electrodes implanted on or under the dura mater, and usually within the patient's brain. Unless the context clearly and expressly indicates otherwise, the term "EEG" shall be used generically herein to refer to both EEG and ECoG signals.

Much of the work on detection has focused on the use of time-domain analysis of EEG signals. See, e.g., J. Gotman, Automatic seizure detection: improvements and evaluation, Electroencephalogr. Clin. Neurophysiol. 1990; 76(4): 317-24. In a typical time-domain detection system, EEG signals are received by one or more implanted electrodes and then processed by a control module, which then is capable of performing an action (intervention, warning, recording, etc.) when an abnormal event is detected.

It is generally preferable to be able to detect and treat a seizure at or near its beginning, or even before it begins. The beginning of a seizure is referred to herein as an "onset." However, it is important to note that there are two general varieties of seizure onsets. A "clinical onset" represents the beginning of a seizure as manifested through observable clinical symptoms, such as involuntary muscle movements or neurophysiological effects such as lack of responsiveness. An "electrographic onset" refers to the beginning of detectable electrographic activity indicative of a seizure. An electrographic onset will frequently occur before the corresponding clinical onset, enabling intervention before the patient suffers symptoms, but that is not always the case. In addition, there are changes in the EEG that occur seconds or even minutes before the electrographic onset that can be identified and used to facilitate intervention before electrographic or clinical onsets occur. This capability would be considered seizure prediction, in contrast to the detection of a seizure or its onset.

In the Gotman system, EEG waveforms are filtered and decomposed into "features" representing characteristics of interest in the waveforms. One such feature is characterized by the regular occurrence (i.e., density) of half-waves exceeding a threshold amplitude occurring in a specified frequency band between approximately 3 Hz and 20 Hz, especially in comparison to background (non-ictal) activity. When such half-waves are detected, it is believed that seizure activity is occurring For related approaches, see also H. Qu and J. Gotman, A seizure warning system for long term epilepsy monitoring, Neurology 1995; 45: 2250-4; and H. Qu and J. Gotman, A Patient-Specific Algorithm for the Detection of Seizure Onset in Long-Term EEG Monitoring: Possible Use as a Warning Device, IEEE Trans. Biomed. Eng. 1997; 44(2): 115-22.

The Gotman articles address half wave characteristics in general, and introduce a variety of measurement criteria, including a ratio of current epoch amplitude to background; average current epoch EEG frequency; average background EEG frequency; coefficient of variation of wave duration; ratio of current epoch amplitude to following time period; average wave amplitude; average wave duration; dominant frequency (peak frequency of the dominant peak); and average power in a main energy zone. These criteria are variously mapped into an n-dimensional space, and whether a seizure is detected depends on the vector distance between the parameters of a measured segment of EEG and a seizure template in that space.

It should be noted that the schemes set forth in the above articles are not tailored for use in an implantable device, and hence typically require more computational ability than would be available in such a device.

U.S. Pat. No. 6,018,682 to Rise describes an implantable seizure warning system that implements a form of the Gotman system. However, the system described therein uses only a single detection modality, namely a count of sharp spike and wave patterns within a timer period. This is accomplished with relatively complex processing, including averaging over time and quantifying sharpness by way of a second derivative of the signal. The Rise patent does not disclose how the signals are processed at a low level, nor does it explain detection criteria in any sufficiently specific level of detail.

A more computationally demanding approach is to transform EEG signals into the frequency domain for rigorous spectrum analysis. See, e.g., U.S. Pat. No. 5,995,868 to Dorfmeister et al., which analyzes the power spectral density of EEG signals in comparison to background characteristics. Although this approach is generally believed to achieve good results, for the most part, its computational expense renders it less than optimal for use in long-term implanted epilepsy monitor and treatment devices. With current technology, the battery life in an implantable device computationally capable of performing the Dorfmeister method would be too short for it to be feasible.

Also representing an alternative and more complex approach is U.S. Pat. No. 5,857,978 to Hively et al., in which various non-linear and statistical characteristics of EEG signals are analyzed to identify the onset of ictal activity. Once more, the calculation of statistically relevant characteristics is not believed to be feasible in an implantable device.

U.S. Pat. No. 6,016,449 to Fischell, et al. (which is hereby incorporated by reference as though set forth in full herein), describes an implantable seizure detection and treatment system. In the Fischell system, various detection methods are possible, all of which essentially rely upon the analysis (either in the time domain or the frequency domain) of processed EEG signals. Fischell's controller is preferably implanted intracranially, but other approaches are also possible, including the use of an external controller. When a seizure is detected, the Fischell system applies responsive electrical stimulation to terminate the seizure, a capability that will be discussed in further detail below.

All of these approaches provide useful information, and in some cases may provide sufficient information for accurate detection and prediction of most imminent epileptic seizures.

However, none of the various implementations of the known approaches provide 100% seizure detection accuracy in a clinical environment.

Two types of detection errors are generally possible. A "false positive," as the term is used herein, refers to a detection of a seizure or ictal activity when no seizure or other abnormal event is actually occurring. Similarly, a "false negative" herein refers to the failure to detect a seizure or ictal activity that actually is occurring or shortly will occur.

In most cases, with all known implementations of the known approaches to detecting abnormal seizure activity solely by monitoring and analyzing EEG activity, when a seizure detection algorithm is tuned to catch all seizures, there will be a significant number of false positives. While it is currently believed that there are minimal or no side effects to limited amounts of over-stimulation (e.g., providing stimulation sufficient to terminate a seizure in response to a false positive), the possibility of accidentally initiating a seizure or increasing the patient's susceptibility to seizures must be considered.

As is well known, it has been suggested that it is possible to treat and terminate seizures by applying electrical stimulation to the brain. See, e.g., U.S. Pat. No. 6,016,449 to Fischell et al., and H. R. Wagner, et al., Suppression of cortical epileptiform activity by generalized and localized ECoG desynchronization, Electroencephalogr. Clin. Neurophysiol. 1975; 39(5): 499-506. And as stated above, it is believed to be beneficial to perform this stimulation only when a seizure (or other undesired neurological event) is occurring or about to occur, as inappropriate stimulation may result in the initiation of seizures.

Furthermore, it should be noted that a false negative (that is, a seizure that occurs without any warning or treatment from the device) will often cause the patient significant discomfort and detriment. Clearly, false negatives are to be avoided.

It has been found to be difficult to achieve an acceptably low level of false positives and false negatives with the level of computational ability available in an implantable device with reasonable battery life.

Preferably, the battery in an implantable device, particularly one implanted intracranially, should last at least several years. There is a substantial risk of complications (such as infection, blood clots, and the overgrowth of scar tissue) and lead failure each time an implanted device or its battery is replaced. Rechargeable batteries have not been found to provide any advantage in this regard, as they are not as efficient as traditional cells, and the additional electronic circuitry required to support the recharging operation contributes to the device's size and complexity. Moreover, there is a need for patient discipline in recharging the device batteries, which would require the frequent transmission of a substantial amount of power over a wireless link and through the patient's skin and other tissue.

As stated above, the detection and prediction of ictal activity has traditionally required a significant amount of computational ability. Moreover, for an implanted device to have significant real-world utility, it is also advantageous to include a number of other features and capabilities. Specifically, treatment (via electrical stimulation or drug infusion) and/or warning (via an audio annunciator, for example), recording of EEG signals for later consideration and analysis, and telemetry providing a link to external equipment are all useful capabilities for an implanted device capable of detecting or predicting epileptiform signals. All of these additional subsystems will consume further power.

Moreover, size is also a consideration. For various reasons, intracranial implants are favored. A device implanted intracranially (or under the scalp) will typically have a lower risk of failure than a similar device implanted pectorally or elsewhere, which require a lead to be run from the device, through the patient's neck to the electrode implantation sites in the patient's head. This lead is also prone to receive additional electromagnetic interference.

As is well known in the art, the computational ability of a processor-controlled system is directly related to both size and power consumption. In accordance with the above considerations, therefore, it would be advantageous to have sufficient detection and prediction capabilities to avoid a substantial number of false positive and false negative detections, and yet consume little enough power (in conjunction with the other subsystems) to enable long battery life. Such an implantable device would have a relatively low-power central processing unit to reduce the electrical power consumed by that portion.

At the current time, there is no known implantable device that is capable of detecting and predicting seizures and yet has adequate battery life and the consequent acceptably low risk factors for use in human patients.

SUMMARY OF THE INVENTION

Accordingly, an implantable device according to the invention for detecting and predicting epileptic seizures includes a relatively low-speed and low-power central processing unit, as well as customized electronic circuit modules in a detection subsystem. As described herein, the detection subsystem also performs prediction, which in the context of the present application is a form of detection that occurs before identifiable clinical symptoms or even obvious electrographic patterns are evident upon inspection. The same methods, potentially with different parameters, are adapted to be used for both detection and prediction. Generally, as described herein, an event (such as an epileptic seizure) may be detected, an electrographic "onset" of such an event (an electrographic indication of an event occurring at the same time as or before the clinical event begins) may be detected (and may be characterized by different waveform observations than the event itself), and a "precursor" to an event (electrographic activity regularly occurring some time before the clinical event) may be detected as predictive of the event.

As described herein and as the terms are generally understood, the present approach is generally not statistical or stochastic in nature. The invention, and particularly the detection subsystem thereof, is specifically adapted to perform much of the signal processing and analysis requisite for accurate and effective event detection. The central processing unit remains in a suspended "sleep" state characterized by relative inactivity a substantial percentage of the time, and is periodically awakened by interrupts from the detection subsystem to perform certain tasks related to the detection and prediction schemes enabled by the device.

Much of the processing performed by an implantable system according to the invention involves operations on digital data in the time domain. Preferably, to reduce the amount of data processing required by the invention, samples at ten-bit resolution are taken at a rate less than or equal to approximately 500 Hz (2 ms per sample).

As stated above, an implantable system according to the invention is capable of accurate and reliable seizure detection and prediction. To accomplish this, the invention employs a combination of signal processing and analysis modalities, including data reduction and feature extraction techniques, mostly implemented as customized digital electronics modules, minimally reliant upon a central processing unit.

In particular, it has been found to be advantageous to utilize two different data reduction methodologies, both of which collect data representative of EEG signals within a sequence of uniform time windows each having a specified duration.

The first data reduction methodology involves the calculation of a "line length function" for an EEG signal within a time window. Specifically, the line length function of a digital signal represents an accumulation of the sample-to-sample amplitude variation in the EEG signal within the time window. Stated another way, the line length function is representative of the variability of the input signal. A constant input signal will have a line length of zero (representative of substantially no variation in the signal amplitude), while an input signal that oscillates between extrema from sample to sample will approach the maximum line length. It should be noted that while the line length function has a physical-world analogue in measuring the vector distance traveled in a graph of the input signal, the concept of line length as treated herein disregards the horizontal (X) axis in such a situation. The horizontal axis herein is representative of time, which is not combinable in any meaningful way in accordance with the invention with information relating to the vertical (Y) axis, generally representative of amplitude, and which in any event would contribute nothing of interest.

The second data reduction methodology involves the calculation of an "area function" represented by an EEG signal within a time window. Specifically, the area function is calculated as an aggregation of the EEG's signal total deviation from zero over the time window, whether positive or negative. The mathematical analogue for the area function defined above is the mathematical integral of the absolute value of the EEG function (as both positive and negative signals contribute to positive area). Once again, the horizontal axis (time) makes no contribution to accumulated energy as treated herein. Accordingly, an input signal that remains around zero will have a small area value, while an input signal that remains around the most-positive or most-negative values will have a high area value.

Both the area and line length functions may undergo linear or non-linear transformations. An example would be to square each amplitude before summing it in the area function. This non-linear operation would provide an output that would approximate the energy of the signal for the period of time it was integrated. Likewise linear and non-linear transformations of the difference between sample values are advantageous in customizing the line length function to increase the effectiveness of the detector for a specific patient.

The central processing unit receives the line length function and area function measurements performed by the detection subsystem, and is capable of acting based on those measurements or their trends.

Feature extraction, specifically the identification of half waves in an EEG signal, also provides useful information. A half wave is an interval between a local waveform minimum and a local waveform maximum; each time a signal "changes directions" (from increasing to decreasing, or vice versa), subject to limitations that will be set forth in further detail below, a new half wave is identified.

The identification of half waves having specific amplitude and duration criteria allows some frequency-driven characteristics of the EEG signal to be considered and analyzed without the need for computationally intensive transformations of normally time-domain EEG signals into the frequency domain. Specifically, the half wave feature extraction capability of the invention identifies those half waves in the input signal having a duration that exceeds a minimum duration criterion and an amplitude that exceeds a minimum amplitude criterion. The number of half waves in a time window meeting those criteria is somewhat representative of the amount of energy in a waveform at a frequency below the frequency corresponding to the minimum duration criterion. And the number of half waves in a time window is constrained somewhat by the duration of each half wave (i.e., if the half waves in a time window have particularly long durations, relatively fewer of them will fit into the time window), that number is highest when a dominant waveform frequency most closely matches the frequency corresponding to the minimum duration criterion.

As stated above, the half waves, line length function, and area function of various EEG signals are calculated by customized electronics modules with minimal involvement by the central processing unit, and are selectively combined by a system according to the invention to provide detection and prediction of seizure activity, so that appropriate action can then be taken.

Accordingly, in one embodiment of the invention, a system according to the invention includes a central processing unit, a detection subsystem located therein that includes a waveform analyzer. The waveform analyzer includes waveform feature analysis capabilities (such as half wave characteristics) as well as window-based analysis capabilities (such as line length and area under the curve), and both aspects are combined to provide enhanced neurological event detection. A central processing unit is used to consolidate the results from multiple channels and coordinate responsive action when necessary.

BRIEF DESCRIPTION OF THE DRAWINGS

These and other objects, features, and advantages of the invention will become apparent from the detailed description below and the accompanying drawings, in which.

DETAILED DESCRIPTION OF THE INVENTION

The invention is described below, with reference to detailed illustrative embodiments. It will be apparent that a system according to the invention may be embodied in a wide variety of forms. Consequently, the specific structural and functional details disclosed herein are representative and do not limit the scope of the invention.

Figure 1:
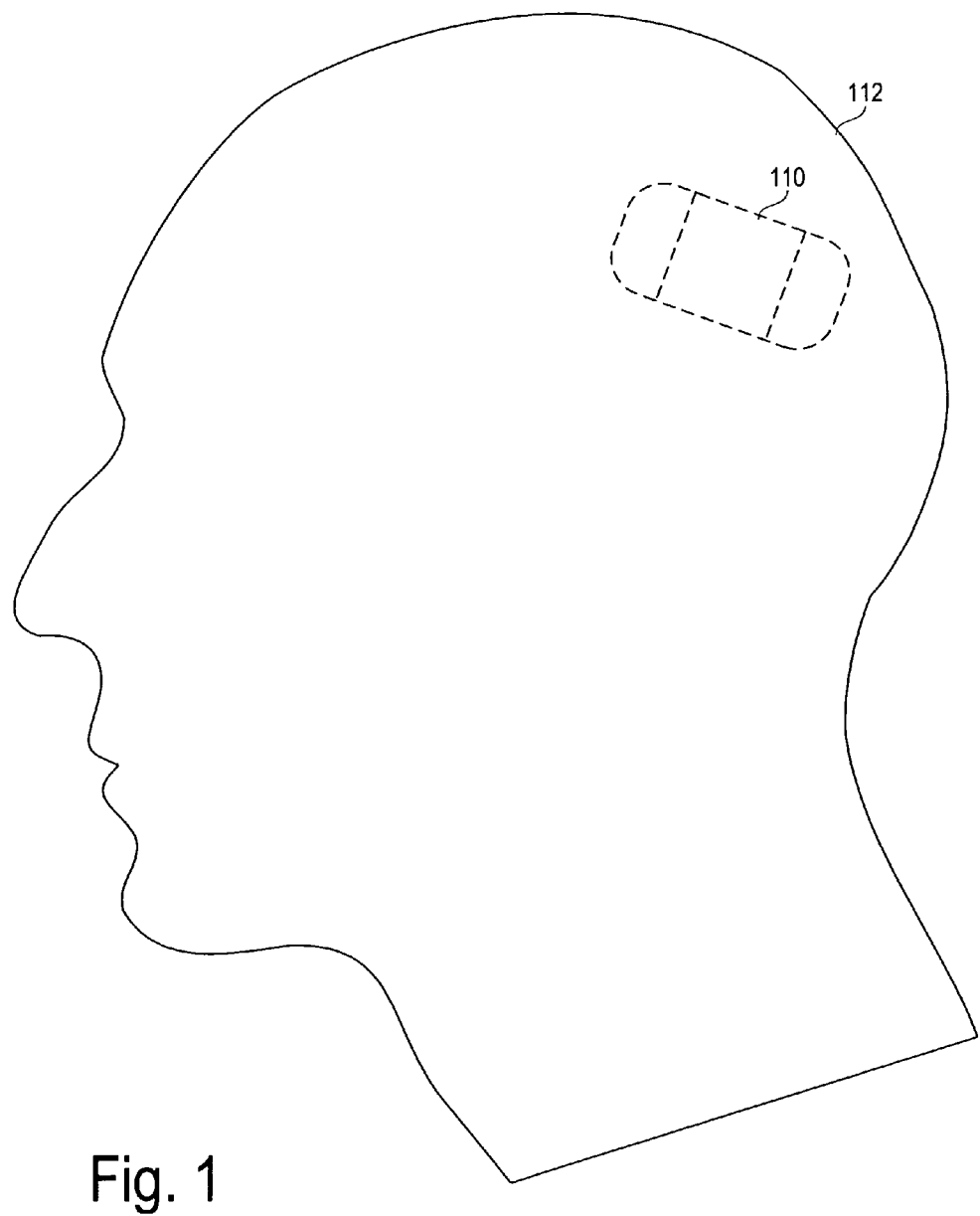
FIG. 1 is a schematic illustration of a patient's head showing the placement of an implantable neurostimulator according to an embodiment of the invention.

FIG. 1 depicts an intracranially implanted device 110 according to the invention, which in one embodiment is a small self-contained responsive neurostimulator. As the term is used herein, a responsive neurostimulator is a device capable of detecting or predicting ictal activity (or other neurological events) and providing electrical stimulation to neural tissue in response to that activity, where the electrical stimulation is specifically intended to terminate the ictal activity, treat a neurological event, prevent an unwanted neurological event from occurring, or lessen the severity or frequency of certain symptoms of a neurological disorder. As disclosed herein, the responsive neurostimulator detects ictal activity by systems and methods according to the invention.

Preferably, an implantable device according to the invention is capable of detecting or predicting any kind of neurological event that has a representative electrographic signature. While the disclosed embodiment is described primarily as responsive to epileptic seizures, it should be recognized that it is also possible to respond to other types of neurological disorders, such as movement disorders (e.g. the tremors characterizing Parkinson's disease), migraine headaches, chronic pain, and neuropsychiatric disorders such as depression. Preferably, neurological events representing any or all of these afflictions can be detected when they are actually occurring, in an onset stage, or as a predictive precursor before clinical symptoms begin.

Figure 2:
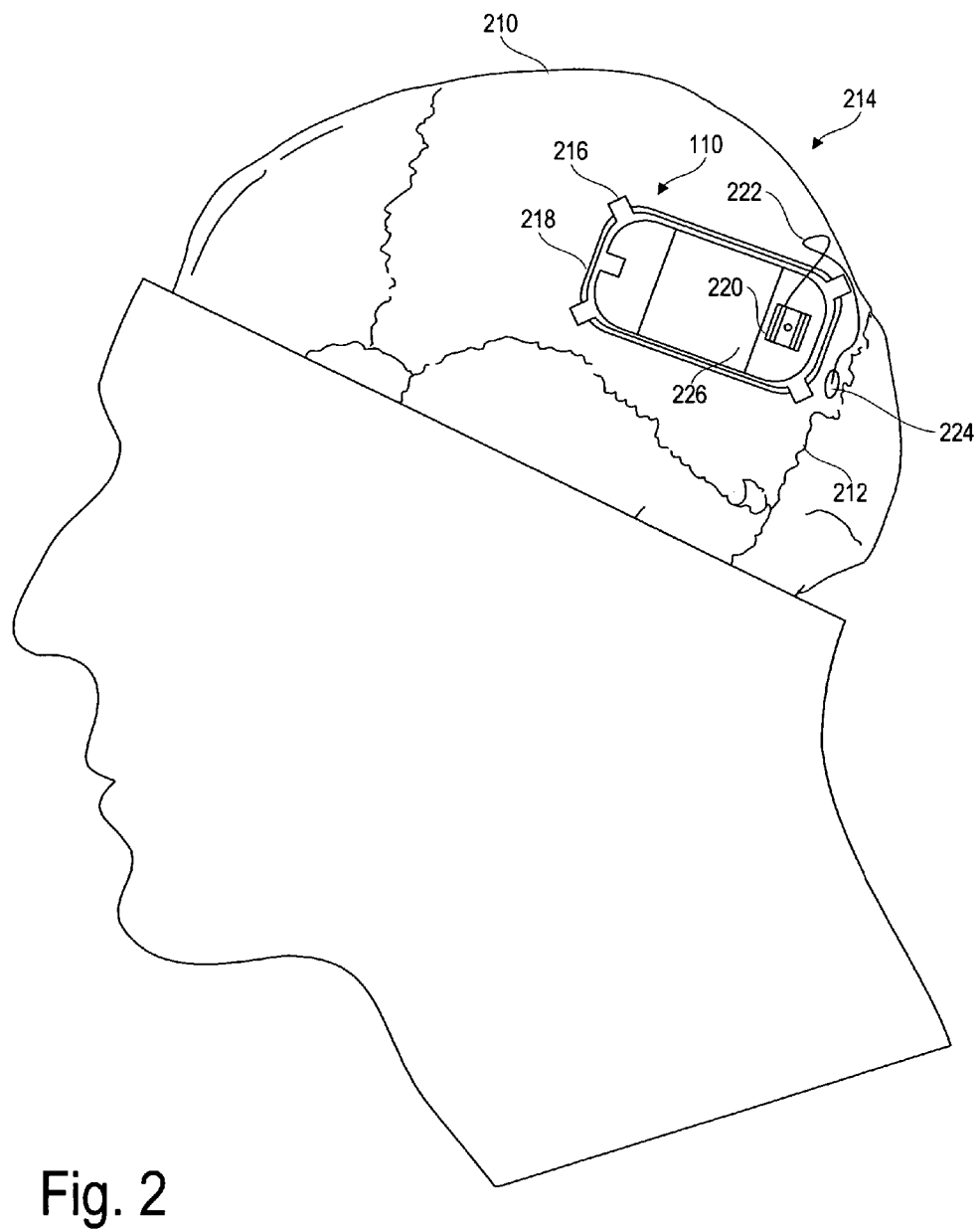
FIG. 2 is a schematic illustration of a patient's cranium showing the implantable neurostimulator of FIG. 1 as implanted, including leads extending to the patient's brain.

In the disclosed embodiment, the neurostimulator is implanted intracranially in a patient's parietal bone 210, in a location anterior to the lambdoidal suture 212 (see FIG. 2). It should be noted, however, that the placement described and illustrated herein is merely exemplary, and other locations and configurations are also possible, in the cranium or elsewhere, depending on the size and shape of the device and individual patient needs, among other factors. The device 110 is preferably configured to fit the contours of the patient's cranium 214. In an alternative embodiment, the device 110 is implanted under the patient's scalp 112 but external to the cranium; it is expected, however, that this configuration would generally cause an undesirable protrusion in the patient's scalp where the device is located. In yet another alternative embodiment, when it is not possible to implant the device intracranially, it may be implanted pectorally (not shown), with leads extending through the patient's neck and between the patient's cranium and scalp, as necessary.

It should be recognized that the embodiment of the device 110 described and illustrated herein is preferably a responsive neurostimulator for detecting and treating epilepsy by detecting seizures or their onsets or precursors, and preventing and/or terminating such epileptic seizures.

In an alternative embodiment of the invention, the device 110 is not a responsive neurostimulator, but is an apparatus capable of detecting neurological conditions and events and performing actions in response thereto. The actions performed by such an embodiment of the device 110 need not be therapeutic, but may involve data recording or transmission, providing warnings to the patient, or any of a number of known alternative actions. Such a device will typically act as a diagnostic device when interfaced with external equipment, as will be discussed in further detail below.

The device 110, as implanted intracranially, is illustrated in greater detail in FIG. 2. The device 110 is affixed in the patient's cranium 214 by way of a ferrule 216. The ferrule 216 is a structural member adapted to fit into a cranial opening, attach to the cranium 214, and retain the device 110.

To implant the device 110, a craniotomy is performed in the parietal bone anterior to the lambdoidal suture 212 to define an opening 218 slightly larger than the device 110. The ferrule 216 is inserted into the opening 218 and affixed to the cranium 214, ensuring a tight and secure fit. The device 110 is then inserted into and affixed to the ferrule 216.

As shown in FIG. 2, the device 110 includes a lead connector 220 adapted to receive one or more electrical leads, such as a first lead 222. The lead connector 220 acts to physically secure the lead 222 to the device 110, and facilitates electrical connection between a conductor in the lead 222 coupling an electrode to circuitry within the device 110. The lead connector 220 accomplishes this in a substantially fluid-tight environment with biocompatible materials.

The lead 222, as illustrated, and other leads for use in a system or method according to the invention, is a flexible elongated member having one or more conductors. As shown, the lead 222 is coupled to the device 110 via the lead connector 220, and is generally situated on the outer surface of the cranium 214 (and under the patient's scalp 112), extending between the device 110 and a burr hole 224 or other cranial opening, where the lead 222 enters the cranium 214 and is coupled to a depth electrode (see FIG. 4) implanted in a desired location in the patient's brain. If the length of the lead 222 is substantially greater than the distance between the device 110 and the burr hole 224, any excess may be urged into a coil configuration under the scalp 112. As described in U.S. Pat. No. 6,006,124 to Fischell, et al., which is hereby incorporated by reference as though set forth in full herein, the burr hole 224 is sealed after implantation to prevent further movement of the lead 222; in an embodiment of the invention, a burr hole cover apparatus is affixed to the cranium 214 at least partially within the burr hole 224 to provide this functionality.

The device 110 includes a durable outer housing 226 fabricated from a biocompatible material. Titanium, which is light, extremely strong, and biocompatible, is used in analogous devices, such as cardiac pacemakers, and would serve advantageously in this context. As the device 110 is self-contained, the housing 226 encloses a battery and any electronic circuitry necessary or desirable to provide the functionality described herein, as well as any other features. As will be described in further detail below, a telemetry coil may be provided outside of the housing 226 (and potentially integrated with the lead connector 220) to facilitate communication between the device 110 and external devices.

The neurostimulator configuration described herein and illustrated in FIG. 2 provides several advantages over alternative designs. First, the self-contained nature of the neurostimulator substantially decreases the need for access to the device 110, allowing the patient to participate in normal life activities. Its small size and intracranial placement causes a minimum of cosmetic disfigurement. The device 110 will fit in an opening in the patient's cranium, under the patient's scalp, with little noticeable protrusion or bulge. The ferrule 216 used for implantation allows the craniotomy to be performed and fit verified without the possibility of breaking the device 110, and also provides protection against the device 110 being pushed into the brain under external pressure or impact. A further advantage is that the ferrule 216 receives any cranial bone growth, so at explant, the device 110 can be replaced without removing any bone screws—only the fasteners retaining the device 110 in the ferrule 216 need be manipulated.

Figure 3:
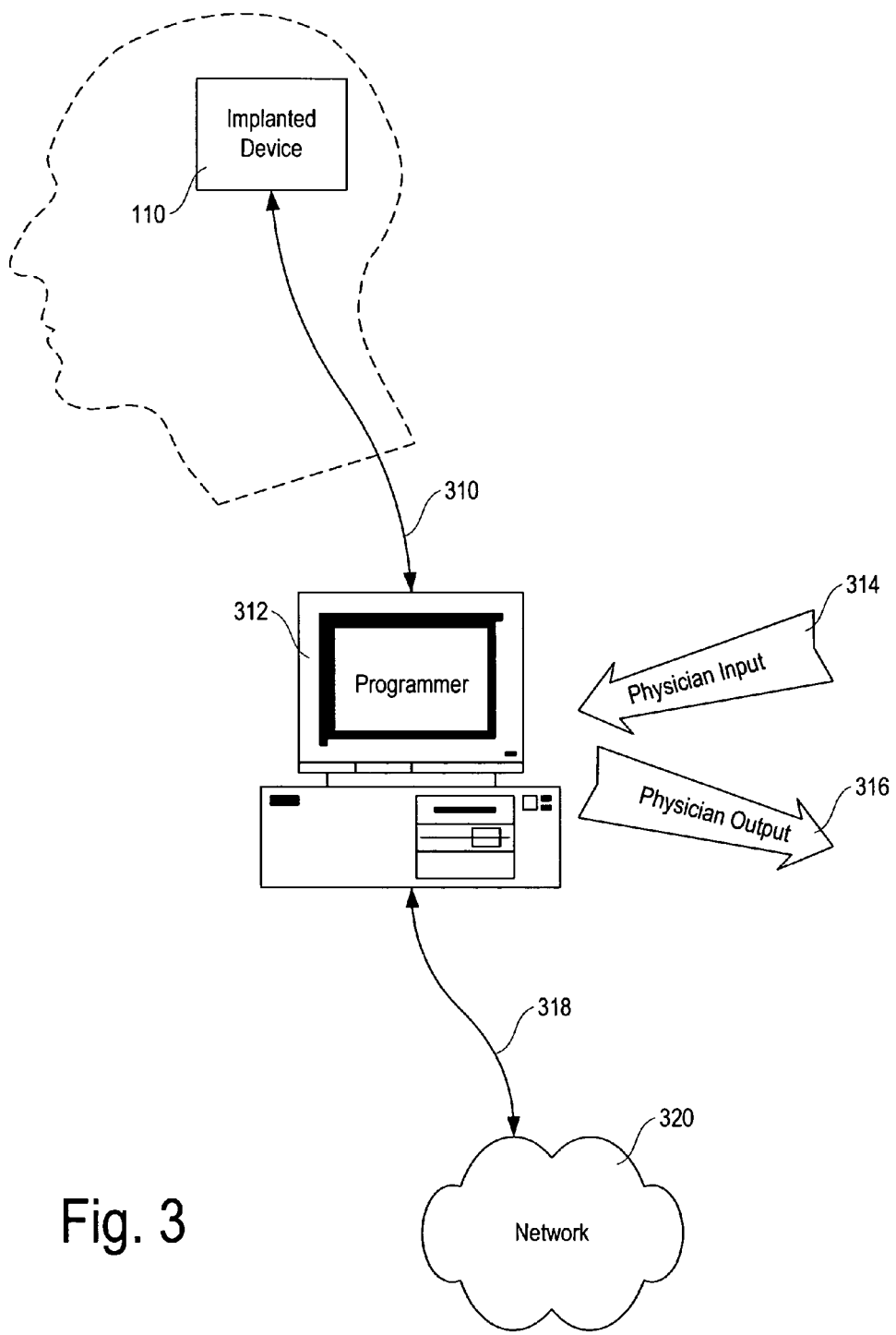
FIG. 3 is a block diagram illustrating context in which an implantable neurostimulator according to the invention is implanted and operated.

As stated above, and as illustrated in FIG. 3, a neurostimulator according to the invention operates in conjunction with external equipment. The device 110 is mostly autonomous (particularly when performing its usual sensing, detection, and stimulation capabilities), but preferably includes a selectable part-time wireless link 310 to external equipment such as a programmer 312. In the disclosed embodiment of the invention, the wireless link 310 is established by moving a wand (or other apparatus) having communication capabilities and coupled to the programmer 312 into range of the device 110. The programmer 312 can then be used to manually control the operation of the device 110, as well as to transmit information to or receive information from the device 110. Several specific capabilities and operations performed by the programmer 312 in conjunction with the device 110 will be described in further detail below.

The programmer 312 is capable of performing a number of advantageous operations in connection with the invention. In particular, the programmer 312 is able to specify and set variable parameters in the device 110 to adapt the function of the device 110 to meet the patient's needs, download or receive data (including but not limited to stored EEG waveforms, parameters, or logs of actions taken) from the device 110 to the programmer 312, upload or transmit program code and other information from the programmer 312 to the device 110, or command the device 110 to perform specific actions or change modes as desired by a physician operating the programmer 312. To facilitate these functions, the programmer 312 is adapted to receive physician input 314 and provide physician output 316; data is transmitted between the programmer 312 and the device 110 over the wireless link 310.

The programmer 312 may be coupled via a communication link 318 to a network 320 such as the Internet. This allows any information downloaded from the device 110, as well as any program code or other information to be uploaded to the device 110, to be stored in a database at one or more data repository locations (which may include various servers and network-connected programmers like the programmer 312). This would allow a patient (and the patient's physician) to have access to important data, including past treatment information and software updates, essentially anywhere in the world that there is a programmer (like the programmer 312) and a network connection.

Figure 4:
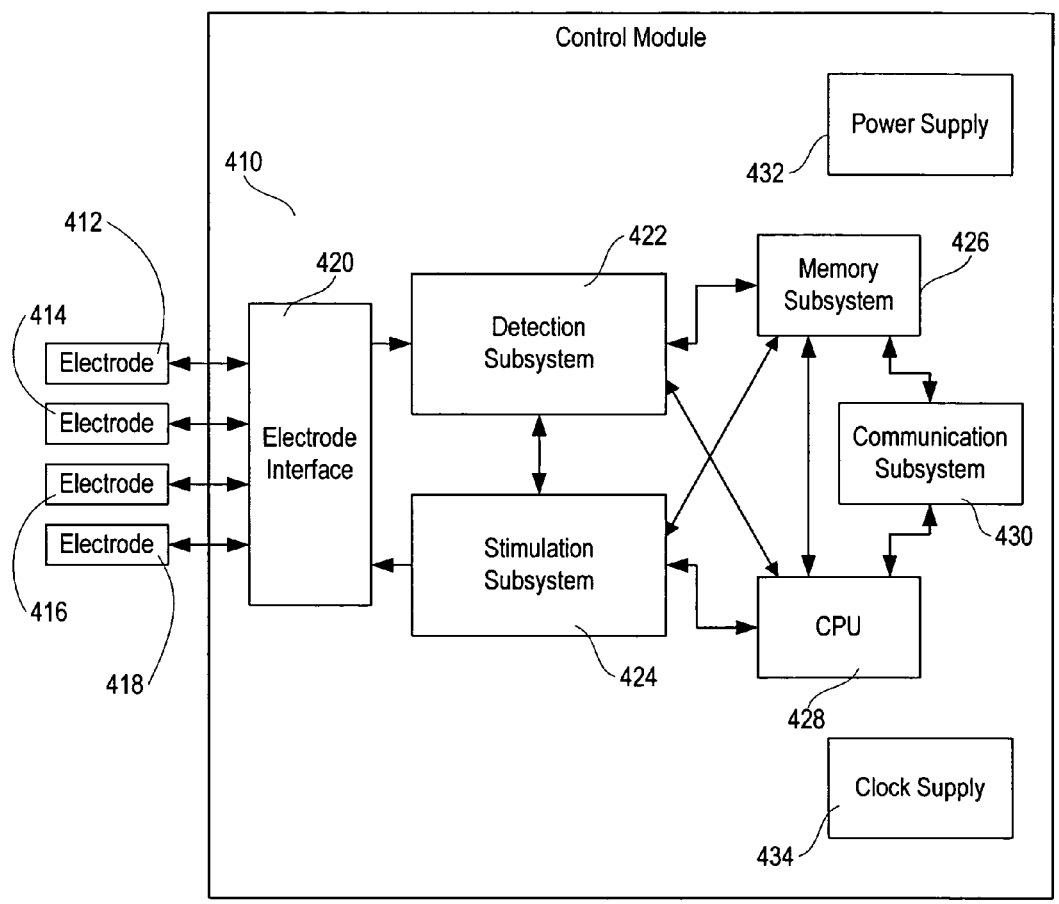
FIG. 4 is a block diagram illustrating the major functional subsystems of an implantable neurostimulator according to the invention.

An overall block diagram of the device 110 used for measurement, detection, and treatment according to the invention is illustrated in FIG. 4. Inside the housing 226 of the device 110 are several subsystems making up a control module 410. The control module 410 is capable of being coupled to a plurality of electrodes 412, 414, 416, and 418 (each of which may be connected to the control module 410 via a lead that is analogous or identical to the lead 222 of FIG. 2) for sensing and stimulation. In the illustrated embodiment, the coupling is accomplished through the lead connector 220 (FIG. 2). Although four electrodes are shown in FIG. 4, it should be recognized that any number is possible, and in the embodiment described in detail below, eight electrodes are used. In fact, it is possible to employ an embodiment of the invention that uses a single lead with at least two electrodes, or two leads each with a single electrode (or with a second electrode provided by a conductive exterior portion of the housing 226 in one embodiment), although bipolar sensing between two closely spaced electrodes on a lead is preferred to minimize common mode signals including noise.

The electrodes 412-418 are connected to an electrode interface 420. Preferably, the electrode interface is capable of selecting each electrode as required for sensing and stimulation; accordingly the electrode interface is coupled to a detection subsystem 422 and a stimulation subsystem 424. The electrode interface also may provide any other features, capabilities, or aspects, including but not limited to amplification, isolation, and charge-balancing functions, that are required for a proper interface with neurological tissue and not provided by any other subsystem of the device 110.

The detection subsystem 422 includes an EEG analyzer function. The EEG analyzer function is adapted to receive EEG signals from the electrodes 412-418, through the electrode interface 420, and to process those EEG signals to identify neurological activity indicative of a seizure, an onset of a seizure, or a precursor to a seizure. One way to implement such EEG analysis functionality is disclosed in detail in U.S. Pat. No. 6,016,449 to Fischell et al., incorporated by reference above; additional inventive methods are described in detail below. The detection subsystem may optionally also contain further sensing and detection capabilities, including but not limited to parameters derived from other physiological conditions (such as electrophysiological parameters, temperature, blood pressure, etc.).

The stimulation subsystem 424 is capable of applying electrical stimulation to neurological tissue through the electrodes 412-418. This can be accomplished in any of a number of different manners. For example, it may be advantageous in some circumstances to provide stimulation in the form of a substantially continuous stream of pulses, or on a scheduled basis. Preferably, therapeutic stimulation is provided in response to abnormal events detected by the EEG analyzer function of the detection subsystem 422. As illustrated in FIG. 4, the stimulation subsystem 424 and the EEG analyzer function of the detection subsystem 422 are in communication; this facilitates the ability of stimulation subsystem 424 to provide responsive stimulation as well as an ability of the detection subsystem 422 to blank the amplifiers while stimulation is being performed to minimize stimulation artifacts. It is contemplated that the parameters of the stimulation signal (e.g., frequency, duration, waveform) provided by the stimulation subsystem 424 would be specified by other subsystems in the control module 410, as will be described in further detail below.

Also in the control module 410 is a memory subsystem 426 and a central processing unit (CPU) 428, which can take the form of a microcontroller. The memory subsystem is coupled to the detection subsystem 422 (e.g., for receiving and storing data representative of sensed EEG signals and evoked responses), the stimulation subsystem 424 (e.g., for providing stimulation waveform parameters to the stimulation subsystem), and the CPU 428, which can control the operation of the memory subsystem 426. In addition to the memory subsystem 426, the CPU 428 is also connected to the detection subsystem 422 and the stimulation subsystem 424 for direct control of those subsystems.

Also provided in the control module 410, and coupled to the memory subsystem 426 and the CPU 428, is a communication subsystem 430. The communication subsystem 430 enables communication between the device 110 (FIG. 1) and the outside world, particularly the external programmer 312 (FIG. 3). As set forth above, the disclosed embodiment of the communication subsystem 430 includes a telemetry coil (which may be situated outside of the housing 226) enabling transmission and reception of signals, to or from an external apparatus, via inductive coupling. Alternative embodiments of the communication subsystem 430 could use an antenna for an RF link or an audio transducer for an audio link.

Rounding out the subsystems in the control module 410 are a power supply 432 and a clock supply 434. The power supply 432 supplies the voltages and currents necessary for each of the other subsystems. The clock supply 434 supplies substantially all of the other subsystems with any clock and timing signals necessary for their operation.

It should be observed that while the memory subsystem 426 is illustrated in FIG. 4 as a separate functional subsystem, the other subsystems may also require various amounts of memory to perform the functions described above and others. Furthermore, while the control module 410 is preferably a single physical unit contained within a single physical enclosure, namely the housing 226 (FIG. 2), it may comprise a plurality of spatially separate units each performing a subset of the capabilities described above. Also, it should be noted that the various functions and capabilities of the subsystems described above may be performed by electronic hardware, computer software (or firmware), or a combination thereof. The division of work between the CPU 428 and the other functional subsystems may also vary—the functional distinctions illustrated in FIG. 4 may not reflect the integration of functions in a real-world system or method according to the invention.

Figure 5:
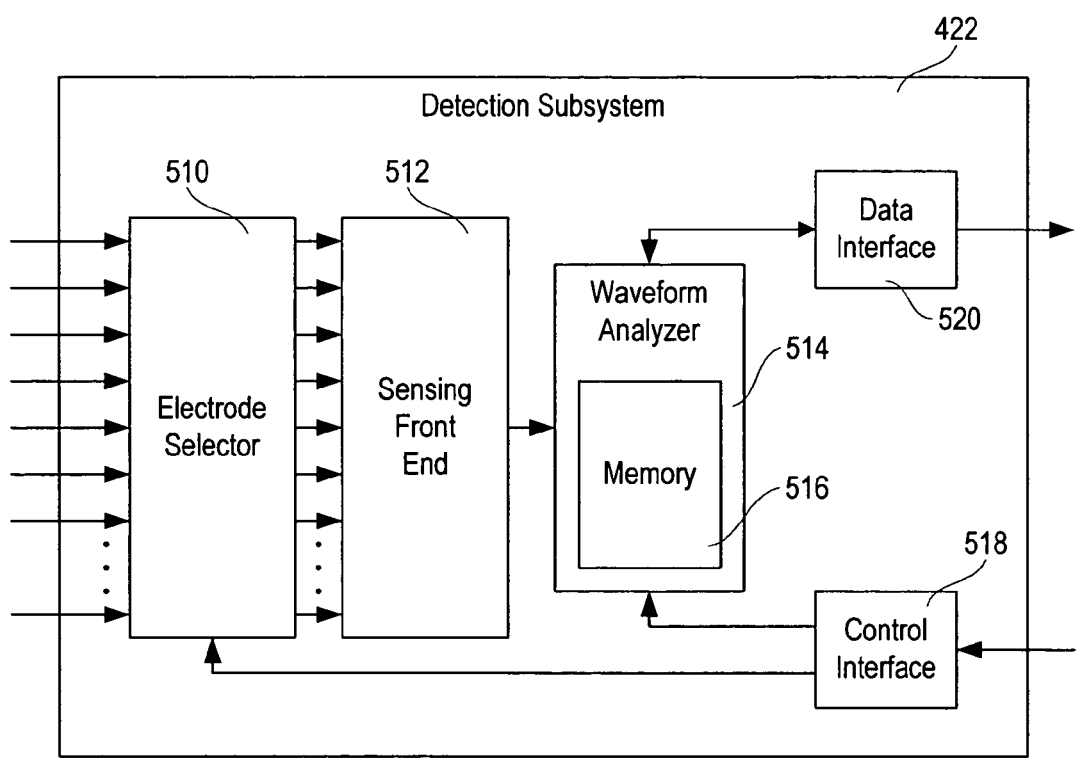
FIG. 5 is a block diagram illustrating the functional components of the detection subsystem of the implantable neurostimulator shown in FIG. 4.

FIG. 5 illustrates details of the detection subsystem 422 (FIG. 4). Inputs from the electrodes 412-418 are on the left, and connections to other subsystems are on the right.

Signals received from the electrodes 412-418 (as routed through the electrode interface 420) are received in an electrode selector 510. The electrode selector 510 allows the device to select which electrodes (of the electrodes 412-418) should be routed to which individual sensing channels of the detection subsystem 422, based on commands received through a control interface 518 from the memory subsystem 426 or the CPU 428 (FIG. 4). Preferably, each sensing channel of the detection subsystem 422 receives a bipolar signal representative of the difference in electrical potential between two selectable electrodes. Accordingly, the electrode selector 510 provides signals corresponding to each pair of selected electrodes (of the electrodes 412-418) to a sensing front end 512, which performs amplification, analog to digital conversion, and multiplexing functions on the signals in the sensing channels. The sensing front end will be described further below in connection with FIG. 6.

A multiplexed input signal representative of all active sensing channels is then fed from the sensing front end 512 to a waveform analyzer 514. The waveform analyzer 514 is preferably a special-purpose digital signal processor (DSP) adapted for use with the invention, or in an alternative embodiment, may comprise a programmable general-purpose DSP. In the disclosed embodiment, the waveform analyzer has its own scratchpad memory area 516 used for local storage of data and program variables when the signal processing is being performed. In either case, the signal processor performs suitable measurement and detection methods described generally above and in greater detail below. Any results from such methods, as well as any digitized signals intended for storage transmission to external equipment, are passed to various other subsystems of the control module 410, including the memory subsystem 426 and the CPU 428 (FIG. 4) through a data interface 520. Similarly, the control interface 518 allows the waveform analyzer 514 and the electrode selector 510 to be in communication with the CPU 428.

Figure 6:
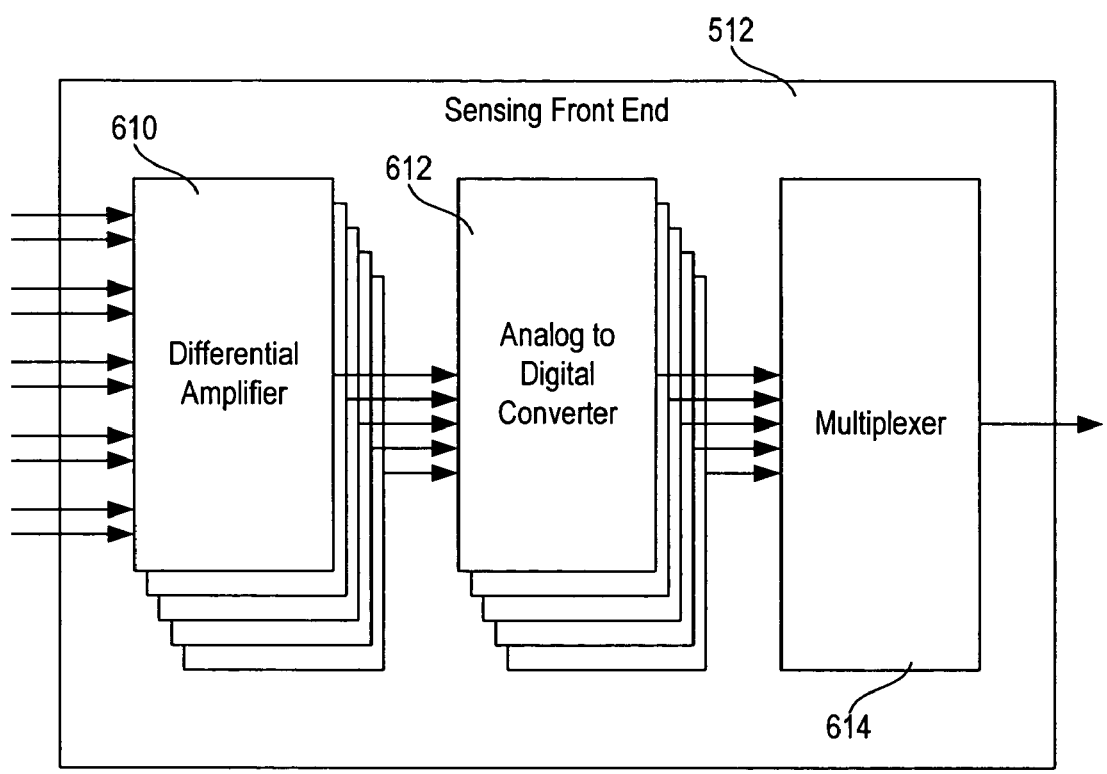
FIG. 6 is a block diagram illustrating the functional components of the sensing front end of the detection subsystem of FIG. 5.

Referring now to FIG. 6, the sensing front end 512 (FIG. 5) is illustrated in further detail. As shown, the sensing front end includes a plurality of differential amplifier channels 610, each of which receives a selected pair of inputs from the electrode selector 510. In a preferred embodiment of the invention, each of differential amplifier channels 610 is adapted to receive or to share inputs with one or more other differential amplifier channels 610 without adversely affecting the sensing and detection capabilities of a system according to the invention. Specifically, in an embodiment of the invention, there are at least eight electrodes, which can be mapped separately to eight differential amplifier channels 610 representing eight different sensing channels and capable of individually processing eight bipolar signals, each of which represents an electrical potential difference between two monopolar input signals received from the electrodes and applied to the sensing channels via the electrode selector 510. For clarity, only five channels are illustrated in FIG. 6, but it should be noted that any practical number of sensing channels may be employed in a system according to the invention.

Each differential amplifier channel 610 feeds a corresponding analog to digital converter (ADC) 612. Preferably, the analog to digital converters 612 are separately programmable with respect to sample rates—in the disclosed embodiment, the ADCs 612 convert analog signals into 10-bit unsigned integer digital data streams at a sample rate selectable between 250 Hz and 500 Hz. In several of the illustrations described below where waveforms are shown, sample rates of 250 Hz are typically used for simplicity. However, the invention shall not be deemed to be so limited, and numerous sample rate and resolution options are possible, with tradeoffs known to individuals of ordinary skill in the art of electronic signal processing. The resulting digital signals are received by a multiplexer 614 that creates a single interleaved digital data stream representative of the data from all active sensing channels. As will be described in further detail below, not all of the sensing channels need to be used at one time, and it may in fact be advantageous in certain circumstances to deactivate certain sensing channels to reduce the power consumed by a system according to the invention.

It should be noted that as illustrated and described herein, a "sensing channel" is not necessarily a single physical or functional item that can be identified in any illustration. Rather, a sensing channel is formed from the functional sequence of operations described herein, and particularly represents a single electrical signal received from any pair or combination of electrodes, as preprocessed by a system according to the invention, in both analog and digital forms. See, e.g., U.S. patent application Ser. No. 09/517,797 to D. Fischell et al., filed on Mar. 2, 2000 and entitled "Neurological Event Detection Using Processed Display Channel Based Algorithms and Devices Incorporating These Procedures," which is hereby incorporated by reference as though set forth in full herein. At times (particularly after the multiplexer 614), multiple sensing channels are processed by the same physical and functional components of the system; notwithstanding that, it should be recognized that unless the description herein indicates to the contrary, a system according to the invention processes, handles, and treats each sensing channel independently.

The interleaved digital data stream is passed from the multiplexer 614, out of the sensing front end 512, and into waveform analyzer 514. The waveform analyzer 514 is illustrated in detail in FIG. 7.

The interleaved digital data stream representing information from all of the active sensing channels is first received by a channel controller 710. The channel controller applies information from the active sensing channels to a number of wave morphology analysis units 712 and window analysis units 714. It is preferred to have as many wave morphology analysis units 712 and window analysis units 714 as possible, consistent with the goals of efficiency, size, and low power consumption necessary for an implantable device. In a presently preferred embodiment of the invention, there are sixteen wave morphology analysis units 712 and eight window analysis units 714, each of which can receive data from any of the sensing channels of the sensing front end 512, and each of which can be operated with different and independent parameters, including differing sample rates, as will be discussed in further detail below.

Each of the wave morphology analysis units 712 operates to extract certain feature information from an input waveform as described below in conjunction with FIGS. 9-11. Similarly, each of the window analysis units 714 performs certain data reduction and signal analysis within time windows in the manner described in conjunction with FIGS. 12-17. Output data from the various wave morphology analysis units 712 and window analysis units 714 are combined via event detector logic 716. The event detector logic 716 and the channel controller 710 are controlled by control commands 718 received from the control interface 518 (FIG. 5).

A "detection channel," as the term is used herein, refers to a data stream including the active sensing front end 512 and the analysis units of the waveform analyzer 514 processing that data stream, in both analog and digital forms. It should be noted that each detection channel can receive data from a single sensing channel; each sensing channel preferably can be applied to the input of any combination of detection channels. The latter selection is accomplished by the channel controller 710. As with the sensing channels, not all detection channels need to be active; certain detection channels can be deactivated to save power or if additional detection processing is deemed unnecessary in certain applications.

In conjunction with the operation of the wave morphology analysis units 712 and the window analysis units 714, a scratchpad memory area 516 is provided for temporary storage of processed data. The scratchpad memory area 516 may be physically part of the memory subsystem 426, or alternatively may be provided for the exclusive use of the waveform analyzer 514. Other subsystems and components of a system according to the invention may also be furnished with local scratchpad memory, if such a configuration is advantageous.

Figure 8:
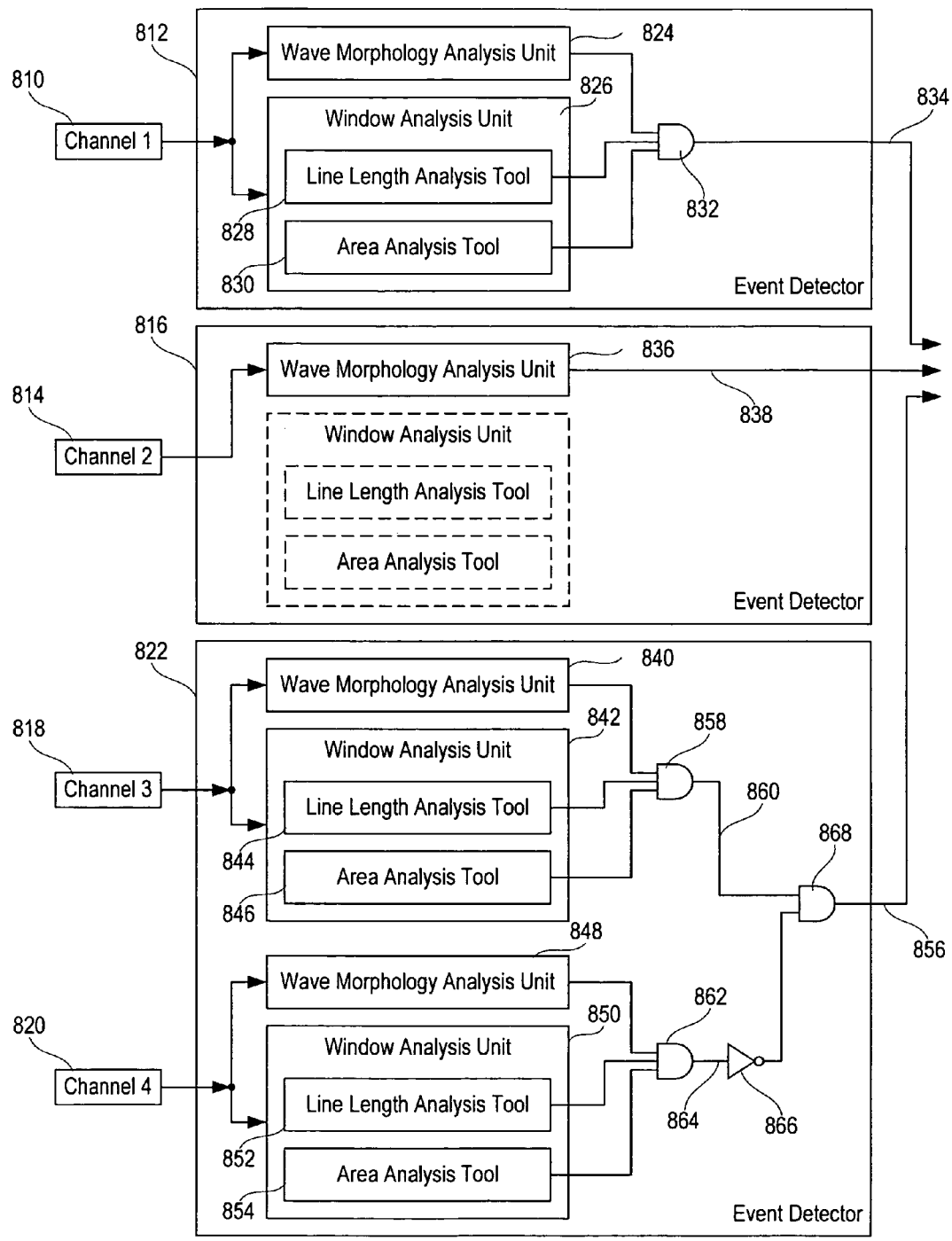
FIG. 8 is a block diagram illustrating the functional arrangement of components of the waveform analysis of the detection subsystem of FIG. 5 in one possible programmed embodiment of the invention.

The operation of the event detector logic 716 is illustrated in detail in the functional block diagram of FIG. 8, in which four exemplary sensing channels are analyzed by three illustrative event detectors.

A first sensing channel 810 provides input to a first event detector 812. While the first event detector 812 is illustrated as a functional block in the block diagram of FIG. 8, it should be recognized that it is a functional block only for purposes of illustration, and may not have any physical counterpart in a device according to the invention. Similarly, a second sensing channel 814 provides input to a second event detector 816, and a third input channel 818 and a fourth input channel 820 both provide input to a third event detector 822.

Figure 7:
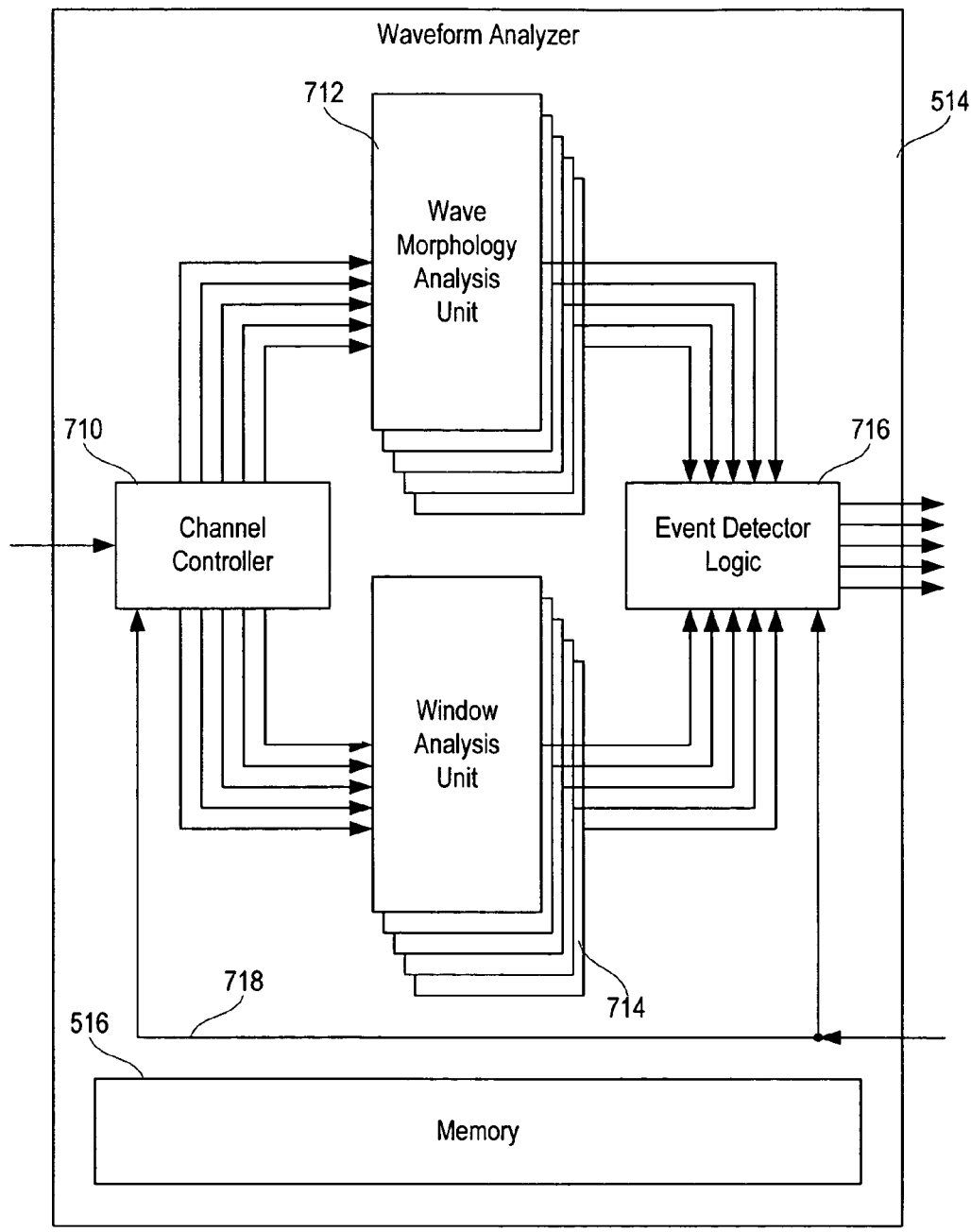
FIG. 7 is a block diagram illustrating the components of the waveform analyzer of the detection subsystem of FIG. 5.

Considering the processing performed by the event detectors 812, 816, and 822, the first input channel 810 feeds a signal to both a wave morphology analysis unit 824 (one of the wave morphology analysis units 712 of FIG. 7) and a window analysis unit 826 (one of the window analysis units 714 of FIG. 7). The window analysis unit 826, in turn, includes a line length analysis tool 828 and an area analysis tool 830. As will be discussed in detail below, the line length analysis tool 828 and the area analysis tool 830 analyze different aspects of the signal from the first input channel 810

Outputs from the wave morphology analysis unit 824, the line length analysis tool 828, and the area analysis tool 830 are combined in a Boolean AND operation 832 and sent to an output 834 for further use by a system according to the invention. For example, if a combination of analysis tools in an event detector identifies several simultaneous (or near-simultaneous) types of activity in an input channel, a system according to the invention may be programmed to perform an action in response thereto. Details of the analysis tools and the combination processes used in event detectors according to the invention will be set forth in greater detail below.

In the second event detector 816, only a wave morphology analysis unit 836 is active. Accordingly, no Boolean operation needs to be performed, and the wave morphology analysis unit 836 directly feeds an event detector output 838.

The third event detector 822 operates on two input channels 818 and 820, and includes two separate detection channels of analysis units: a first wave morphology analysis unit 840 and a first window analysis unit 842, the latter including a first line length analysis tool 844 and a first area analysis tool 846; and a second wave morphology analysis unit 848 and a second window analysis unit 850, the latter including a second line length analysis tool 852 and a second area analysis tool 854. The two detection channels of analysis units are combined to provide a single event detector output 856.

In the first detection channel of analysis units 840 and 842, outputs from the first wave morphology analysis unit 840, the first line length analysis tool 844, and the first area analysis tool 846 are combined via a Boolean AND operation 858 into a first detection channel output 860. Similarly, in the second detection channel of analysis units 848 and 850, outputs from the second wave morphology analysis unit 848, the second line length analysis tool 852, and the second area analysis tool 854 are combined via a Boolean AND operation 862 into a second detection channel output 864. In the illustrated embodiment of the invention, the second detection channel output 864 is invertible with selectable Boolean logic inversion 866 before it is combined with the first detection channel output 860. Subsequently, the first detection channel output 860 and the second detection channel output 864 are combined with a Boolean AND operation 868 to provide a signal to the output 856. In an alternative embodiment, a Boolean OR operation is used to combine the first detection channel output 860 and the second detection channel output 864.

In one embodiment of the invention, the second detection channel (analysis units 848 and 850) represents a "qualifying channel" with respect to the first detection channel (analysis units 840 and 842). In general, a qualifying channel allows a detection to be made only when both channels are in concurrence with regard to detection of an event. For example, a qualifying channel can be used to indicate when a seizure has "generalized," i.e. spread through a significant portion of a patient's brain. To do this, the third input channel 818 and the fourth input channel 820 are configured to receive EEG waveforms from separate amplifier channels coupled to electrodes in separate parts of the patient's brain (e.g., in opposite hemispheres). Accordingly, then, the Boolean AND operation 868 will indicate a detection only when the first detection output 860 and the second detection output 864 both indicate the presence of an event (or, when Boolean logic inversion 866 is present, when the first detection output 860 indicates the presence of an event while the second detection output 864 does not). As will be described in further detail below, the detection outputs 860 and 864 can be provided with selectable persistence (i.e., the ability to remain triggered for some time after the event is detected), allowing the Boolean AND combination 868 to be satisfied even when there is not precise temporal synchronization between detections on the two channels.

It should be appreciated that the concept of a "qualifying channel" allows the flexible configuration of a device 110 according to the invention to achieve a number of advantageous results. In addition to the detection of generalization, as described above, a qualifying channel can be configured, for example, to detect noise so a detection output is valid only when noise is not present, to assist in device configuration in determining which of two sets of detection parameters is preferable (by setting up the different parameters in the first detection channel and the second detection channel, then replacing the Boolean AND combination with a Boolean OR combination), or to require a specific temporal sequence of detections (which would be achieved in software by the CPU 428 after a Boolean OR combination of detections). There are numerous other possibilities.

The outputs 834, 838, and 856 of the event detectors are preferably represented by Boolean flags, and as described below, provide information for the operation of a system according to the invention.

While FIG. 8 illustrates four different sensing channels providing input to four separate detection channels, it should be noted that a maximally flexible embodiment of the present invention would allow each sensing channel to be connected to one or more detection channels. It may be advantageous to program the different detection channels with different settings (e.g., thresholds) to facilitate alternate "views" of the same sensing channel data stream.

Figure 9:
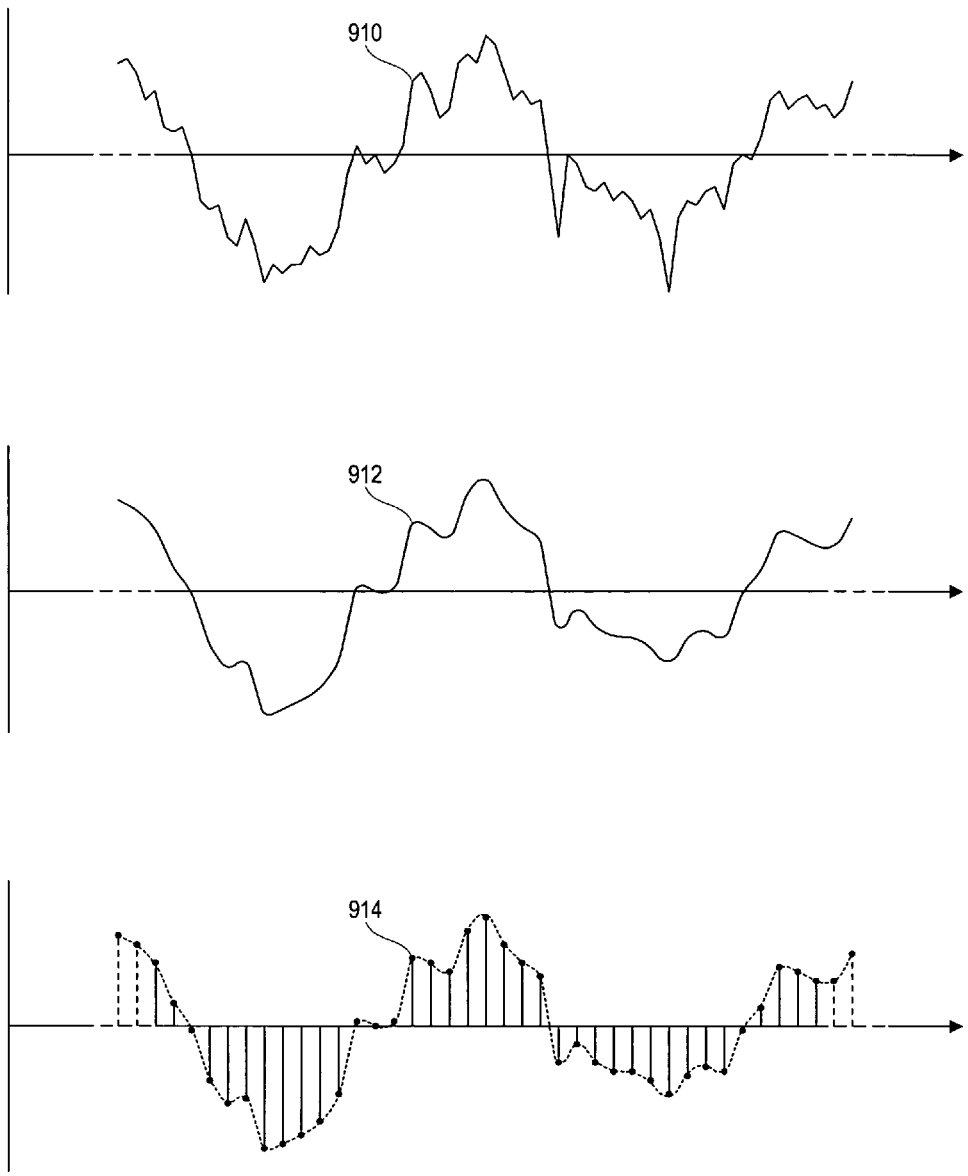
FIG. 9 is a graph of an exemplary EEG signal, illustrating decomposition of the signal into time windows and samples.

FIG. 9 illustrates three representative waveforms of the type expected to be manipulated by a system according to the invention. It should be noted, however, that the waveforms illustrated in FIG. 9 are illustrative only, and are not intended to represent any actual data. The first waveform 910 is representative of an unprocessed electroencephalogram (EEG) or electrocorticogram (ECoG) waveform having a substantial amount of variability; the illustrated segment has a duration of approximately 160 ms and a dominant frequency (visible as the large-scale crests and valleys) of approximately 12.5 Hz. It will be recognized that the first waveform is rather rough and peaky; there is a substantial amount of high-frequency energy represented therein.

The second waveform 912 represents a filtered version of the original EEG waveform 910. As shown, most of the high-frequency energy has been eliminated from the signal, and the waveform 912 is significantly smoother. In the disclosed embodiment of the invention, this filtering operation is performed in the sensing front end 512 before the analog to digital converters 612 (FIG. 6).

The filtered waveform 912 is then sampled by one of the analog to digital converters 612; this operation is represented graphically in the third waveform 914 of FIG. 9. As illustrated, a sample rate used in an embodiment of the invention is 250 Hz (4 ms sample duration), resulting in approximately 40 samples over the illustrated 160 ms segment. As is well known in the art of digital signal processing, the amplitude resolution of each sample is limited; in the disclosed embodiment, each sample is measured with a resolution of 10 bits (or 1024 possible values). As is apparent upon visual analysis of the third waveform, the dominant frequency component has a wavelength of approximately 20 samples, which corresponds to the dominant frequency of 12.5 Hz.

Figure 10:
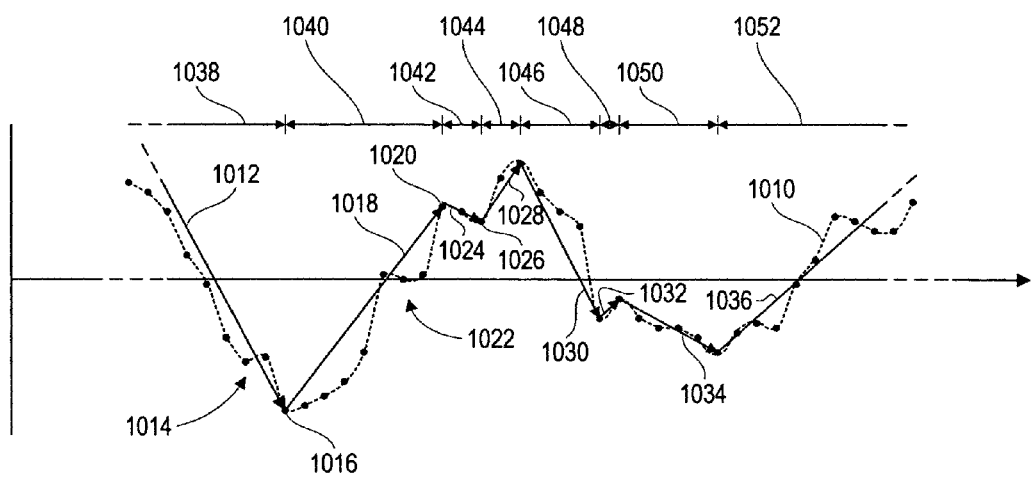
FIG. 10 is a graph of the exemplary EEG signal of FIG. 9, illustrating the extraction of half waves from the signal.

Referring now to FIG. 10, the processing of the wave morphology analysis units 712 is described in conjunction with a filtered and sampled waveform 1010 of the type illustrated as the third waveform 914 of FIG. 9.

In a first half wave 1012, which is partially illustrated in FIG. 10 (the starting point occurs before the illustrated waveform segment 1010 begins), the waveform segment 1010 is essentially monotonically decreasing, except for a small first perturbation 1014. Accordingly, the first half wave 1012 is represented by a vector from the starting point (not shown) to a first local extremum 1016, where the waveform starts to move in the opposite direction. The first perturbation 1014 is of insufficient amplitude to be considered a local extremum, and is disregarded by a hysteresis mechanism (discussed in further detail below). A second half wave 1018 extends between the first local extremum 1016 and a second local extremum 1020. Again, a second perturbation 1022 is of insufficient amplitude to be considered an extremum. Likewise, a third half wave 1024 extends between the second local extremum 1020 and a third local extremum 1026; this may appear to be a small perturbation, but is greater in amplitude than a selected hysteresis threshold. The remaining half waves 1028, 1030, 1032, 1034, and 1036 are identified analogously. As will be discussed in further detail below, each of the identified half waves 1012, 1018, 1024, 1028, 1030, 1032, 1034, and 1036 has a corresponding duration 1038, 1040, 1042, 1044, 1046, 1048, 1050, and 1052, respectively, and analogously, a corresponding amplitude determined from the relative positions of each half wave's starting point and ending point along the vertical axis, and a slope direction, increasing or decreasing.

In a method performed according to the invention, it is particularly advantageous to allow for a programmable hysteresis setting in identifying the ends of half waves. In other words, as explained above, the end of an increasing or decreasing half wave might be prematurely identified as a result of quantization (and other) noise, low-amplitude signal components, and other perturbing factors, unless a small hysteresis allowance is made before a reversal of waveform direction (and a corresponding half wave end) is identified. Hysteresis allows for insignificant variations in signal level inconsistent with the signal's overall movement to be ignored without the need for extensive further signal processing such as filtering. Without hysteresis, such small and insignificant variations might lead to substantial and gross changes in where half waves are identified, leading to unpredictable results.

Figure 11:
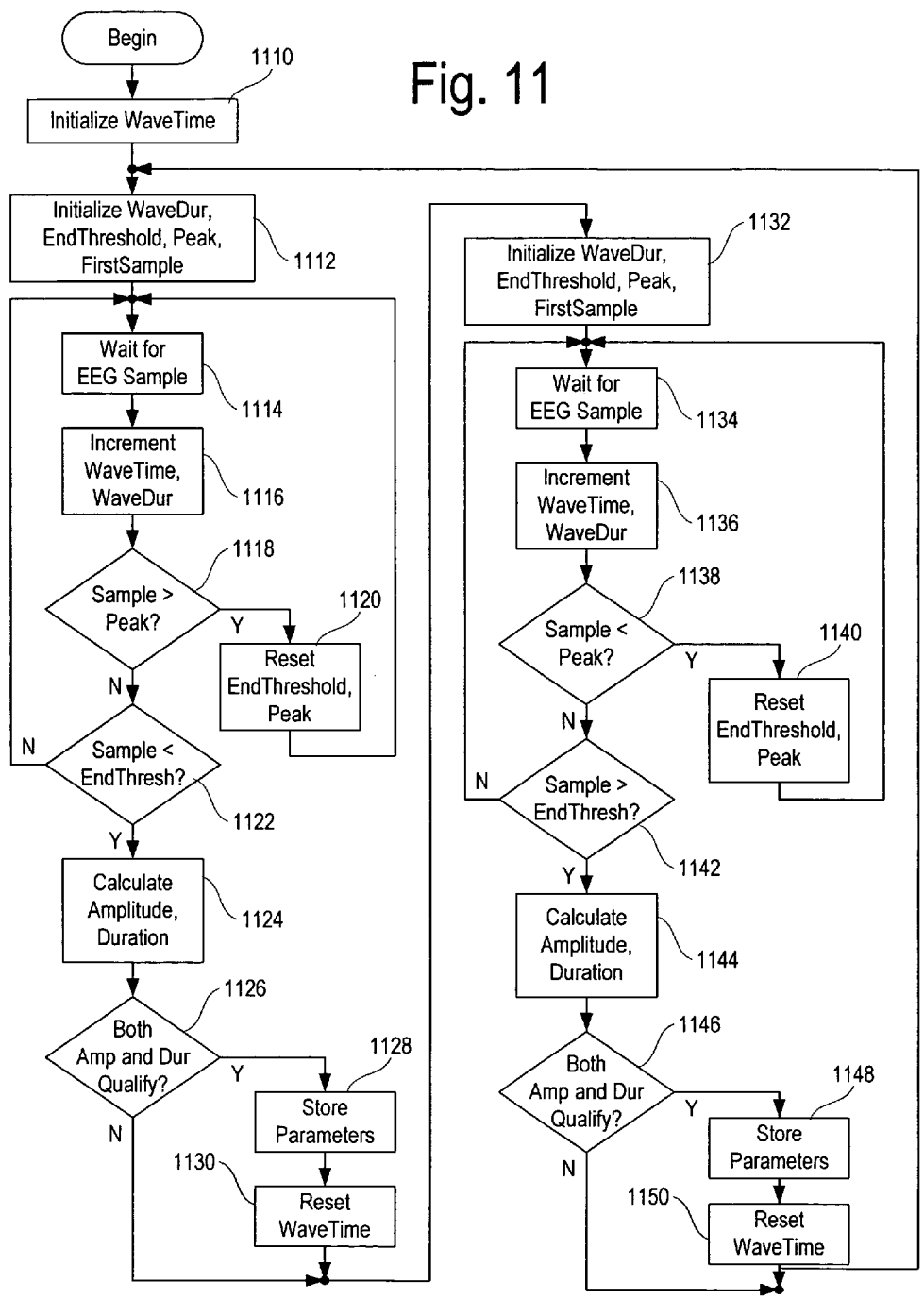
FIG. 11 is a flow chart illustrating the process performed by hardware functional components of the waveform analyzer of FIG. 7 in extracting half waves as illustrated in FIG. 10.

The processing steps performed with regard to the waveform 1010 and half waves of FIG. 10 are set forth in FIG. 11. The method begins by identifying an increasing half wave (with an ending amplitude higher than the starting amplitude, as in the second half wave 1018 of FIG. 10). To do this, a variable corresponding to half wave time is first initialized to zero (step 1110); then half wave duration, ending threshold, peak amplitude, and first sample value are all initialized (step 1112). Specifically, the half wave duration value is set to zero; the peak amplitude and first sample values are set to the amplitude value of the last observed sample, which as described above is a value having 10-bit precision; and the ending threshold is set to the last observed sample minus a small preset hysteresis value. After waiting for a measurement of the current EEG sample (step 1114), the half wave time and half wave duration variables are incremented (step 1116). If the current EEG sample has an amplitude greater than the peak amplitude (step 1118), then the amplitude of the half wave is increasing (or continues to increase). Accordingly, the ending threshold is reset to be the current EEG sample's amplitude minus the hysteresis value, and the peak is reset to the current EEG sample's amplitude (step 1120), and the next sample is awaited (step 1114).

If the current EEG sample has an amplitude less than the ending threshold (step 1122), then the hysteresis value has been exceeded, and a local extremum has been identified. Accordingly, the end of the increasing half wave has been reached, and the amplitude and duration of the half wave are calculated (step 1124). The amplitude is equal to the peak amplitude minus the first sample value; the duration is equal to the current half wave duration. Otherwise, the next ample is awaited (step 1114).

If both the amplitude and the duration qualify by exceeding corresponding preset thresholds (step 1126), then the amplitude, duration, half wave time, half wave direction (increasing) are stored in a buffer (step 1128), and the half wave time is reset to zero (step 1130).

At the conclusion of the increasing half wave, the process continues by initializing wave duration, the ending threshold, the peak amplitude, and the first sample value (step 1132). Wave duration is set to zero, the ending threshold is set to the last sample value plus the hysteresis value, the peak amplitude and the first sample value are set to the most recent sample value.

After waiting for a measurement of the current EEG sample (step 1134), the half wave time and half wave duration variables are incremented (step 1136). If the current EEG sample has an amplitude lower than the peak amplitude (step 1138), then the amplitude of the half wave is decreasing (or continues to decrease). Accordingly, the ending threshold is reset to be the current EEG sample's amplitude plus the hysteresis value, the peak is reset to the current EEG sample's amplitude (step 1140), and the next sample is awaited (step 1134).

If the current EEG sample has an amplitude greater than the ending threshold (step 1142), then the hysteresis value has been exceeded, and a local extremum has been identified. Accordingly, the end of the decreasing half wave has been reached, and the amplitude and duration of the half wave are calculated (step 1144). The amplitude is equal to the first sample value minus the peak amplitude, and the duration is equal to the current half wave duration. Otherwise, the next EEG sample is awaited (step 1134).

If both the amplitude and the duration qualify by exceeding corresponding preset thresholds (step 1146), then the amplitude, duration, half wave time, half wave direction (decreasing) are stored in a buffer (step 1148), and the half wave time is reset to zero (step 1150). It should be noted that, in the context of this specification, the term "exceed" in regard to a threshold value means to meet a specified criterion. Generally, to exceed a threshold herein is to have a numeric value greater than or equal to the threshold, although other interpretations (such as greater than, or less than, or less than or equal to, depending on the context) may be applicable and are deemed to be within the scope of the invention.

At the conclusion of the decreasing half wave, further half waves are then identified by repeating the process from step 1112. As half wave detection is an ongoing and continuous process, this procedure preferably does not exit, but may be suspended from time to time when conditions or device state call for it, e.g. when the device is inactive or when stimulation is being performed. Once suspended in accordance with the invention, the procedure should recommence with the first initialization step 1110.

Accordingly, the process depicted in FIG. 11 stores parameters corresponding to qualified half waves, including their directions, durations, amplitudes, and the elapsed time between adjacent qualified half waves (i.e. the half wave time variable). In the disclosed embodiment of the invention, to reduce power consumption, this procedure is performed in custom electronic hardware; it should be clear that the operations of FIG. 11 are performed in parallel for each active instance of the wave morphology analysis units 712 (FIG. 7). It should also be noted, however, that certain software can also be used to advantageous effect in this context.

Figure 12:
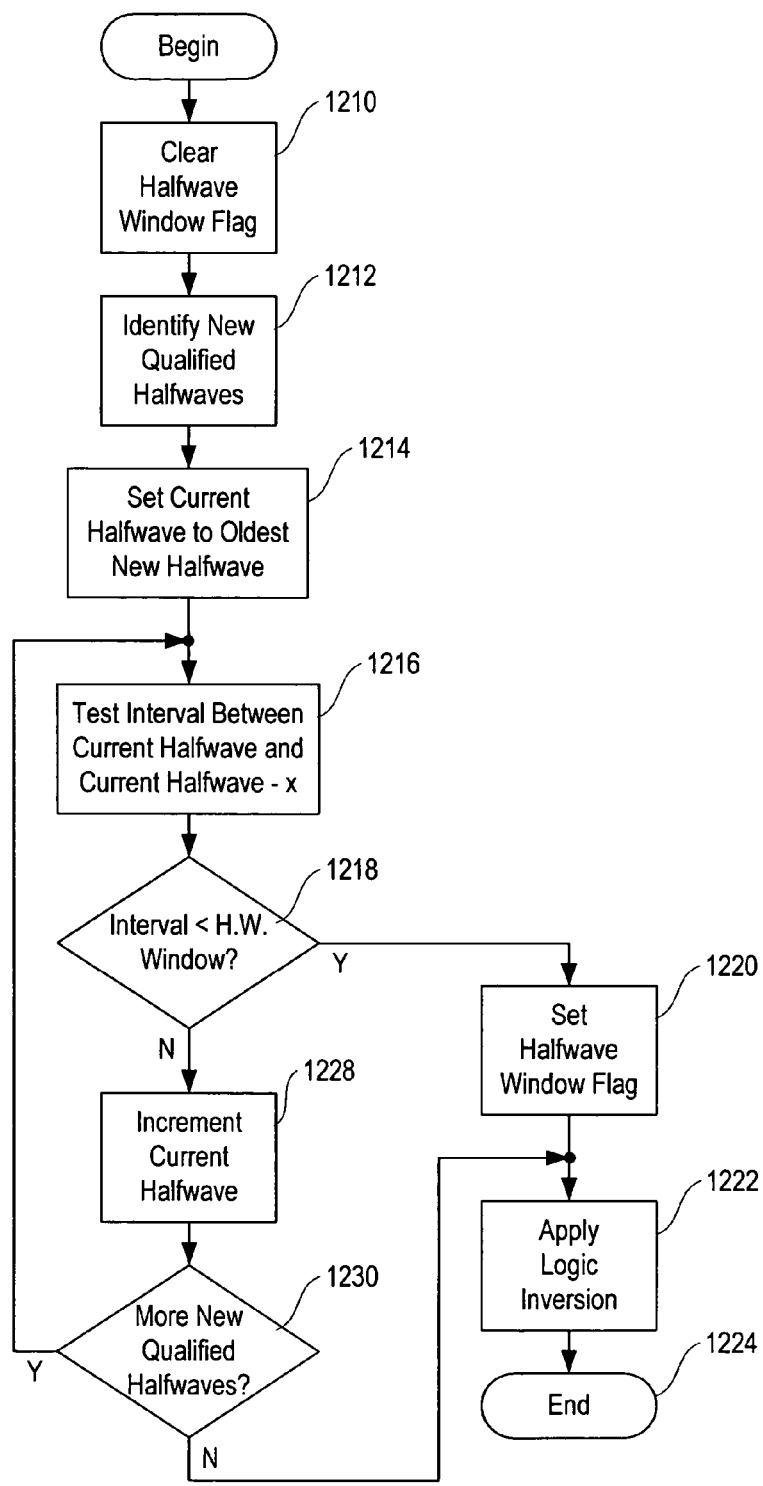
FIG. 12 is a flow chart illustrating the process performed by software in the central processing unit in extracting and analyzing half waves from an EEG signal.

This stored information is used in the software process illustrated in FIG. 12, which is performed on a periodic basis, preferably once every processing window (a recurring time interval that is either fixed or programmable) by a system according to the invention. Consistent with the other analysis tools described herein, the duration of an exemplary processing window is in one embodiment of the invention 128 ms, which corresponds to 32 samples at a 250 Hz sampling rate.

Each time the software process of FIG. 12 is invoked, the half wave window flag is first cleared (step 1210). Any qualified half waves identified by the process set forth in FIG. 11 that are newly identified since the last invocation of the procedure (i.e., all qualified half waves that ended within the preceding processing window) are identified (step 1212). A "current half wave" pointer is set to point to the oldest qualified half wave identified in the most recent processing window (step 1214). The time interval between the current half wave and the prior x half waves is then measured (step 1216), where x is a specified minimum number of half waves (preferably a programmable value) to be identified within a selected half wave time window (the duration of which is another programmable value) to result in the possible detection of a neurological event. If the time interval is less than the duration of the half wave time window (step 1218), then the half wave window flag is set (step 1220), logic inversion is selectively applied (step 1222), and the procedure ends (step 1224). Logic inversion, a mechanism for determining whether an analysis unit is triggered by the presence or absence of a condition, is explained in greater detail below. Otherwise, the current half wave pointer is incremented to point to the next new half wave (step 1228), and if there are no more new half waves (step 1230), logic inversion is applied if desired (step 1222), and the procedure ends (step 1224). Otherwise, the next time interval is tested (step 1216) and the process continues from there.

Logic inversion allows the output flag for the wave morphology analysis unit (or any other analyzer) to be selectively inverted. If logic inversion is configured to be applied to an output of a particular analysis unit, then the corresponding flag will be clear when the detection criterion (e.g., number of qualified half waves) is met, and set when the detection criterion is not met. This capability provides some additional flexibility in configuration, facilitating detection of the absence of certain signal characteristics when, for example, the presence of those characteristics is the norm.

Figure 13:
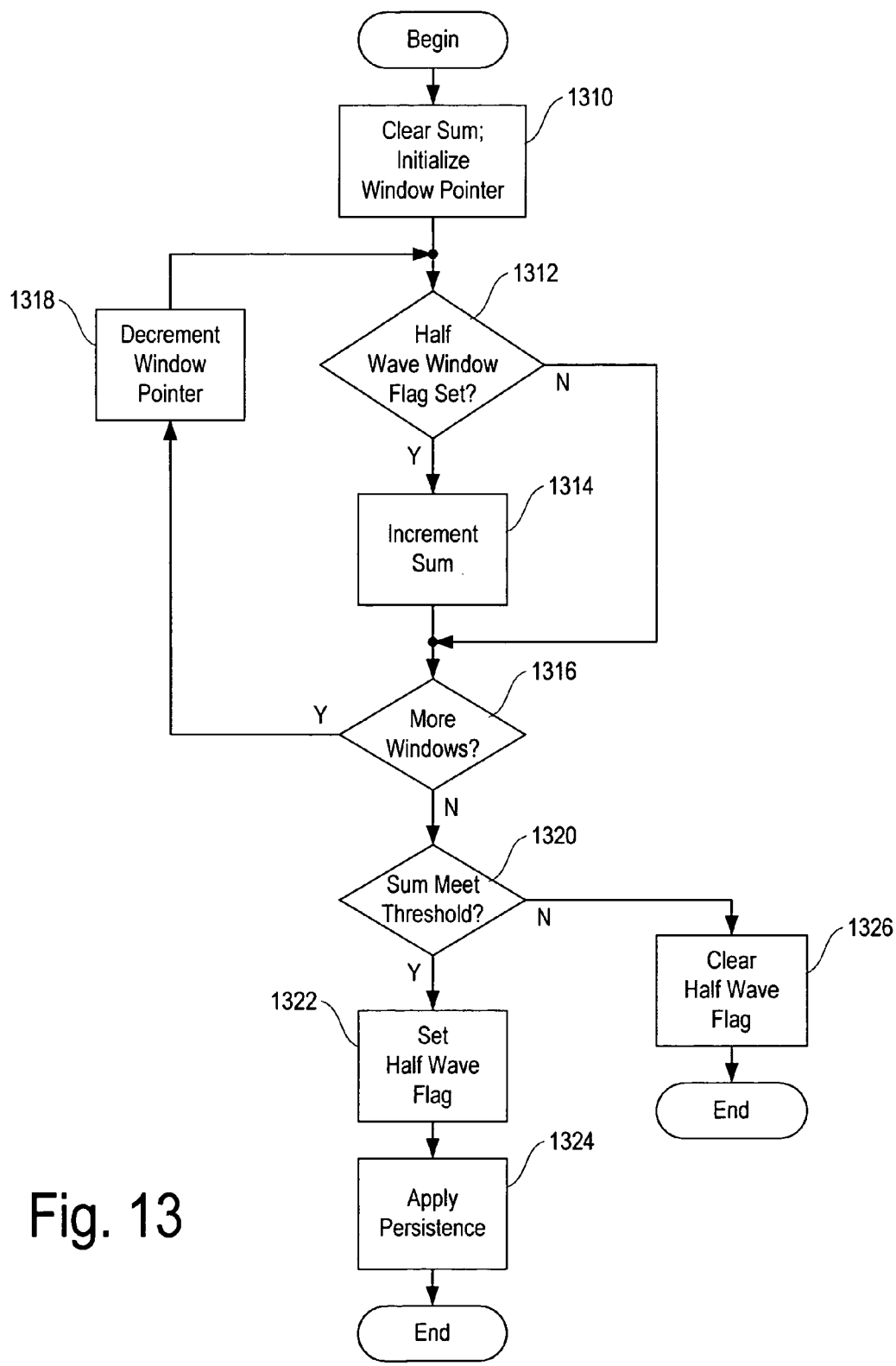
FIG. 13 is a flow chart illustrating the process performed by software in the central processing unit in the application of an X of Y criterion to half wave windows.

In a preferred embodiment of the invention, the half wave window flag (set in step 1220) indicates whether a sufficient number of qualified half waves occur over an interval ending in the most recent processing window. To reduce the occurrence of spurious detections, an X of Y criterion is applied, causing the wave morphology analysis unit to trigger only if a sufficient number of qualified half waves occur in X of the Y most recent processing windows, where X and Y are parameters individually adjustable for each analysis tool. This process is illustrated in FIG. 13.

Initially, a sum (representing recent processing windows having the half wave window flag set) is cleared to zero and a current window pointer is initialized to point to the most recent processing window (step 1310). If the half wave window flag corresponding to the current window pointer is set (step 1312), then the sum is incremented (step 1314). If there are more processing windows to examine (for an X of Y criterion, a total of Y processing windows, including the most recent, should be considered) (step 1316), then the window pointer is decremented (step 1318) and the flag testing and sum incrementing steps (steps 1312-1314) are repeated.

After Y windows have been considered, if the sum of windows having set half wave window flags meets the threshold X (step 1320), then the half wave analysis flag is set (step 1322), persistence (described below) is applied (step 1324), and the procedure is complete. Otherwise, the half wave analysis flag is cleared (step 1326).

Persistence, another per-analysis-tool setting, allows the effect of an event detection (a flag set) to persist beyond the end of the detection window in which the event occurs. In the disclosed system according to the invention, persistence may be set anywhere from one second to fifteen seconds (though other settings are possible), so if detections with multiple analysis tools do not all occur simultaneously (though they should still occur within a fairly short time period), a Boolean combination of flags will still yield positive results. Persistence can also be used with a single analysis tool to smooth the results.

When the process of FIG. 13 is completed, the half wave analysis flag (set or cleared in steps 1322 and 1326, respectively) indicates whether an event has been detected in the corresponding channel of the wave morphology analysis units 712, or stated another way, whether a sufficient number of qualified half waves have appeared in X of the Y most recent processing windows. Although in the disclosed embodiment, the steps of FIGS. 12 and 13 are performed in software, it should be recognized that some or all of those steps can be performed using custom electronics, if it proves advantageous in the desired application to use such a configuration.

Figure 14:
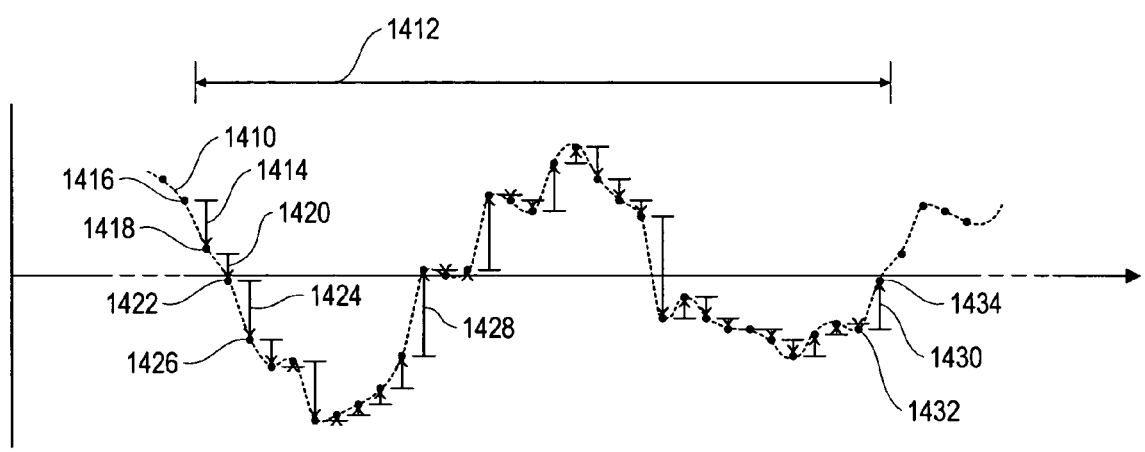
FIG. 14 is a graph of the exemplary EEG signal of FIG. 9, illustrating the calculation of a line length function.

FIG. 14 illustrates the waveform of FIG. 9, further depicting line lengths identified within a time window. The time window used with respect to FIGS. 14-16 may be different from the half wave processing window described above in connection with FIGS. 12-13, but in a preferred embodiment, refers to the same time intervals. From an implementation standpoint, a single device interrupt upon the conclusion of each processing window allows all of the analysis tools to perform the necessary corresponding software processes; the line length analysis process of FIG. 16 (described below) is one such example. A waveform 1410 is a filtered and otherwise pre-processed EEG signal as received in one of the window analysis units 714 from the sensing front end 512. As discussed above, line lengths are considered within time windows. As illustrated in FIG. 14, the duration of an exemplary window 1412 is 32 samples, which is equivalent to 128 ms at a 250 Hz sampling rate.

The total line length for the window 1412 is the sum of the sample-to-sample amplitude differences within that window 1412. For example, the first contribution to the line length within the window 1412 is a first amplitude difference 1414 between a previous sample 1416 occurring immediately before the window 1412 and a first sample 1418 occurring within the window 1412. The next contribution comes from a second amplitude difference 1420 between the first sample 1418 and a second sample 1422; a further contribution 1424 comes from a third amplitude difference between the second sample 1422 and a third sample 1426; and so on. At the end of the window 1412, the final contribution to the line length comes from a last amplitude difference 1430 between a second-last sample 1432 in the window 1412 and a last sample 1434 in the window 1412. Note that all line lengths, whether increasing or decreasing in direction, are accumulated as positive values by the invention; accordingly, a decreasing amplitude difference 1414 and an increasing amplitude difference 1428 both contribute to a greater line length.

As illustrated herein, and as discussed in detail above, there are thirty-two samples within the window 1412. The illustrated window 1412 has a duration of 128 ms, and accordingly, the illustrated sample rate is 250 Hz. It should be noted, however, that alternate window durations and sample rates are possible and considered to be within the scope of the present invention.

Figure 15:
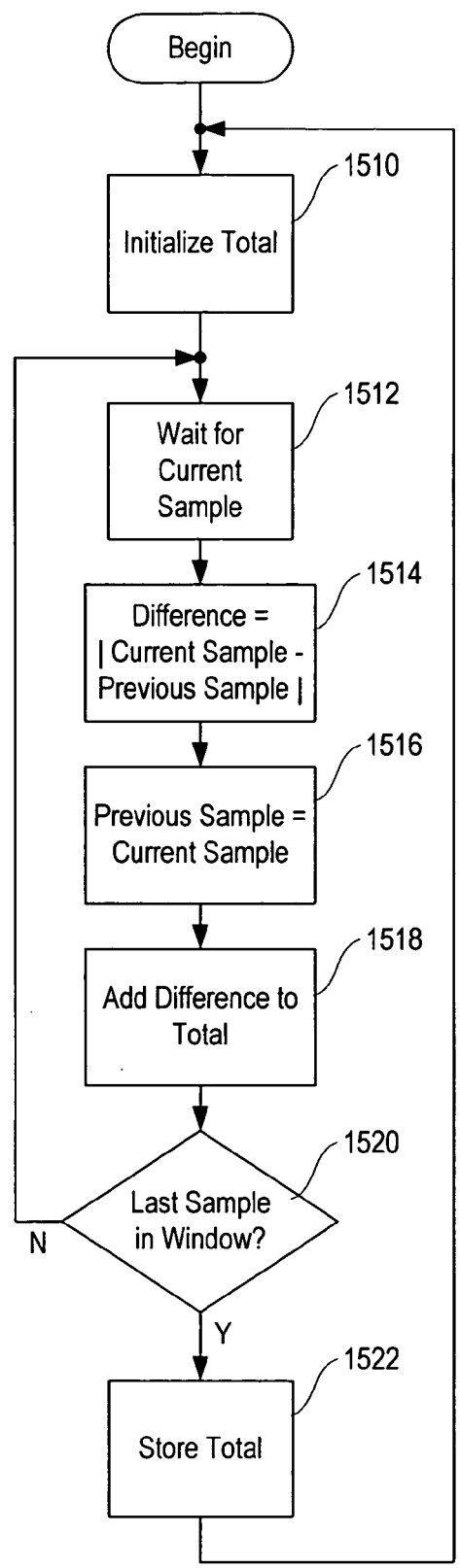
FIG. 15 is a flow chart illustrating the process performed by hardware functional components of the waveform analyzer of FIG. 7 in calculating the line length function as illustrated in FIG. 14.

The line lengths illustrated in FIG. 14 are calculated as shown by the flow chart of FIG. 15, which is invoked at the beginning of a time window. Initially, a line length total variable is initialized to zero (step 1510). The current sample is awaited (step 1512), and the absolute value of the amplitude difference between the current sample and the previous sample (which, when considering the first sample in a window, may come from the last sample in a previous window) is measured (step 1514).

In various alternative embodiments of the invention, either the measured difference (as calculated in step 1514, described above), or the sample values used to calculate the difference may be mathematically transformed in useful nonlinear ways. For example, it may be advantageous in certain circumstances to calculate the difference between adjacent samples using the squares of the sample values, or to calculate the square of the difference between sample values, or both. It is contemplated that other transformations (such as square root, exponentiation, logarithm, and other nonlinear functions) might also be advantageous in certain circumstances. Whether or not to perform such a transformation and the nature of any transformation to be performed are preferably programmable parameters of the device 110.

For use in the next iteration, the previous sample is replaced with the value of the current sample (step 1516), and the calculated absolute value is added to the total (step 1518). If there are more samples remaining in the window 1412 (step 1520), another current sample is awaited (step 1512) and the process continues. Otherwise, the line length calculation for the window 1412 is complete, and the total is stored (step 1522), the total is re-initialized to zero (step 1510), and the process continues.

As with the half wave analysis method set forth above, the line length calculation does not need to terminate; it can be free-running yet interruptible. If the line length calculation is restarted after having been suspended, it should be re-initialized and restarted at the beginning of a window. This synchronization can be accomplished through hardware interrupts.

Figure 16:
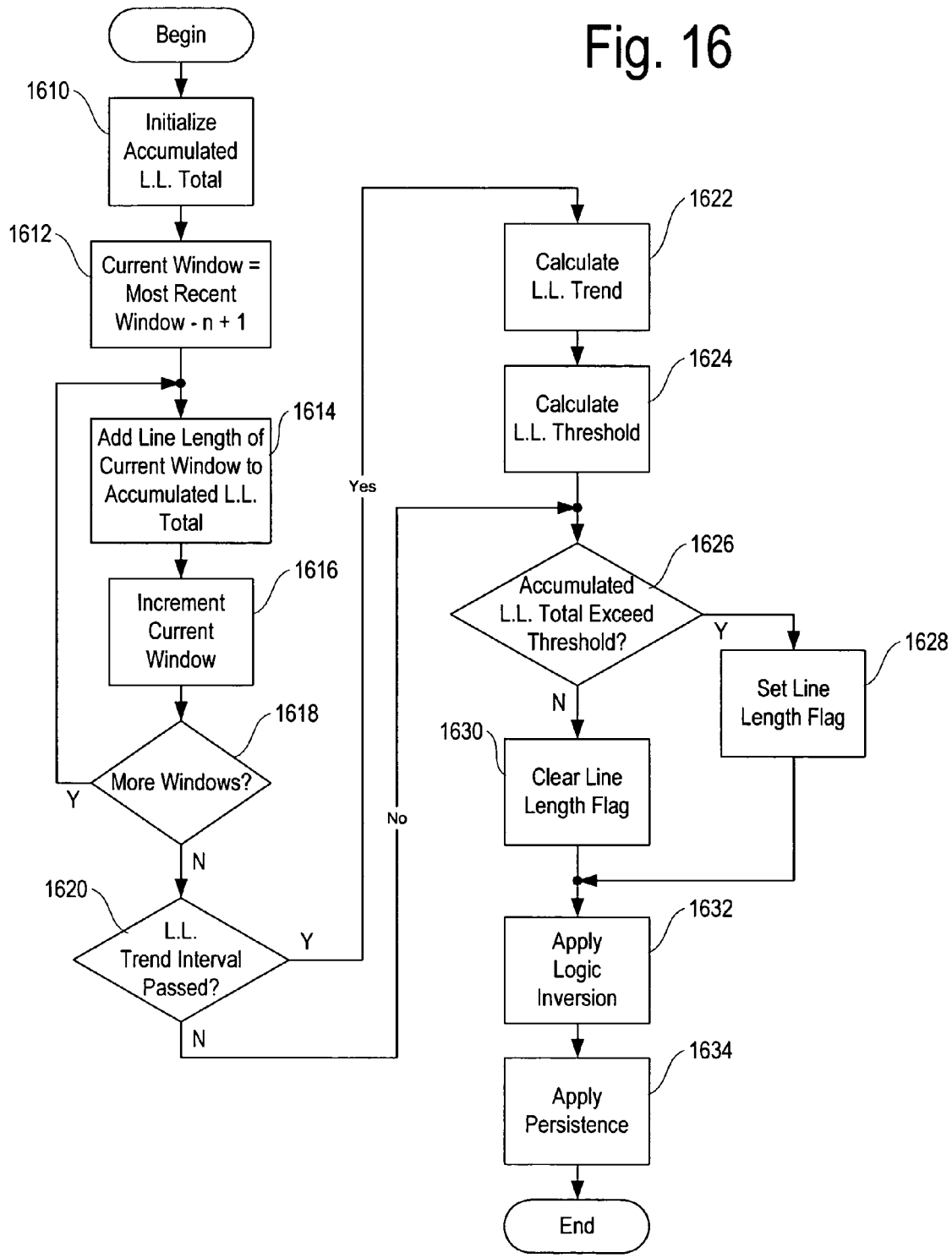
FIG. 16 is a flow chart illustrating the process performed by software in the central processing unit in calculating and analyzing the line length function of an EEG signal.

The line lengths calculated as shown in FIG. 15 are then processed as indicated in the flow chart of FIG. 16, which is performed after each window 1412 is calculated and stored (step 1522).

The process begins by calculating a running accumulated line length total over a period of n time windows. Where n>1, the effect is that of a sliding window; in an alternative embodiment an actual sliding window processing methodology may be used. First, the accumulated total is initialized to zero (step 1610). A current window pointer is set to indicate the $n^{th}$-last window, i.e., the window (n−1) windows before the most recent window (step 1612). The line length of the current window is added to the total (step 1614), the current window pointer is incremented (step 1616), and if there are more windows between the current window pointer and the most recent (last) window (step 1618), the adding and incrementing steps (1614-1616) are repeated. Accordingly, by this process, the resulting total includes the line lengths for each of the n most recent windows.

In the disclosed embodiment of the invention, the accumulated total line length is compared to a dynamic threshold, which is based on a trend of recently observed line lengths. The trend is recalculated regularly and periodically, after each recurring line length trend interval (which is preferably a fixed or programmed time interval). Each time the line length trend interval passes (step 1620), the line length trend is calculated or updated (step 1622). In a presently preferred embodiment of the invention, this is accomplished by calculating a normalized moving average of several trend samples, each of which represents several consecutive windows of line lengths. A new trend sample is taken and the moving average is recalculated upon every line length trend interval. The number of trend samples used in the normalized moving average and the number of consecutive windows of line length measurements per trend sample are preferably both fixed or programmable values.

After the line length trend has been calculated, the line length threshold is calculated (step 1624) based on the new line length trend. In the disclosed embodiment of the invention, the threshold may be set as either a percentage of the line length trend (either below 100% for a threshold that is lower than the trend, or above 100% for a threshold that is higher than the trend) or alternatively a fixed numeric offset from the line length trend (either negative for a threshold that is lower than the trend, or positive for a threshold that is higher than the trend). It should be observed that other methods for deriving a numeric threshold from a numeric trend are possible and deemed to be within the scope of the invention.

The first time the process of FIG. 16 is performed, there is generally no line length trend against which to set a threshold. Accordingly, for the first several passes through the process (until a sufficient amount of EEG data has been processed to establish a trend), the threshold is essentially undefined and the line length detector should not return a positive detection. Some "settling time" is required to establish trends and thresholds before a detection can be made.

If the accumulated line length total exceeds the calculated threshold (step 1626), then a flag is set (step 1628) indicating a line-length-based event detection on the current window analysis unit channel 714. As described above, in the disclosed embodiment of the invention, the threshold is dynamically calculated from a line length trend, but alternatively, the threshold may be static, either fixed or programmed into the device 110. If the accumulated line length total does not exceed the threshold, the flag is cleared (step 1630). Once the line length flag has been either set or cleared, logic inversion is applied (step 1632), persistence is applied (step 1634), and the procedure terminates.

The resulting persistent line length flag indicates whether the threshold has been exceeded within one or more windows over a time period corresponding to the line length flag persistence. As will be discussed in further detail below, line length event detections can be combined with the half wave event detections, as well as any other applicable detection criteria according to the invention.

Figure 17:
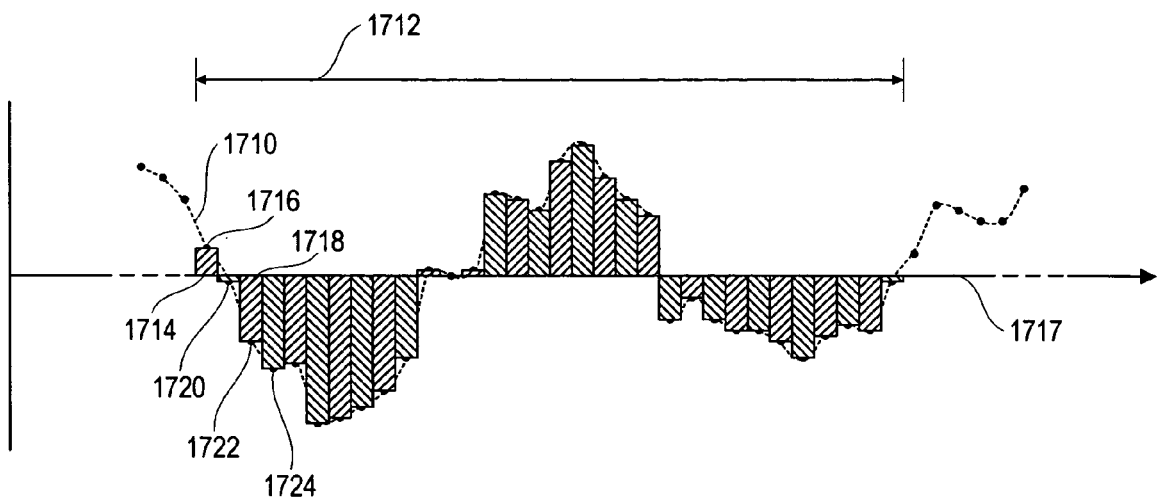
FIG. 17 is a graph of the exemplary EEG signal of FIG. 9, illustrating the calculation of an area function.

FIG. 17 illustrates the waveform of FIG. 9 with area under the curve identified within a window. Area under the curve, which in some circumstances is somewhat representative of a signal's energy (though energy of a waveform is more accurately represented by the area under the square of a waveform), is another detection criterion in accordance with the invention.

The total area under the curve represented by a waveform 1710 within the window 1712 is equal to the sum of the absolute values of the areas of each rectangular region of unit width vertically bounded by the horizontal axis and the sample. For example, the first contribution to the area under the curve within the window 1712 comes from a first region 1714 between a first sample 1716 and a baseline 1717. A second contribution to the area under the curve within the window 1712 comes from a second region 1718, including areas between a second sample 1720 and the baseline 1717. There are similar regions and contributions for a third sample 1722 and the baseline 1717, a fourth sample 1724 and the baseline 1717, and so on. It should be observed that the region widths are not important—the area under each sample can be considered the product of the sample's amplitude and a unit width, which can be disregarded. In a similar manner, each region is accumulated and added to the total area under the curve within the window 1712. Although the concept of separate rectangular regions is a useful construct for visualizing the idea of area under a curve, it should be noted that a process for calculating area need not partition areas into regions as shown in FIG. 17—it is only necessary to accumulate the absolute value of the waveform's amplitude at each sample, as the unit width of each region can be disregarded. The process for doing this will be set forth in detail below in connection with FIG. 18.

Figure 18:
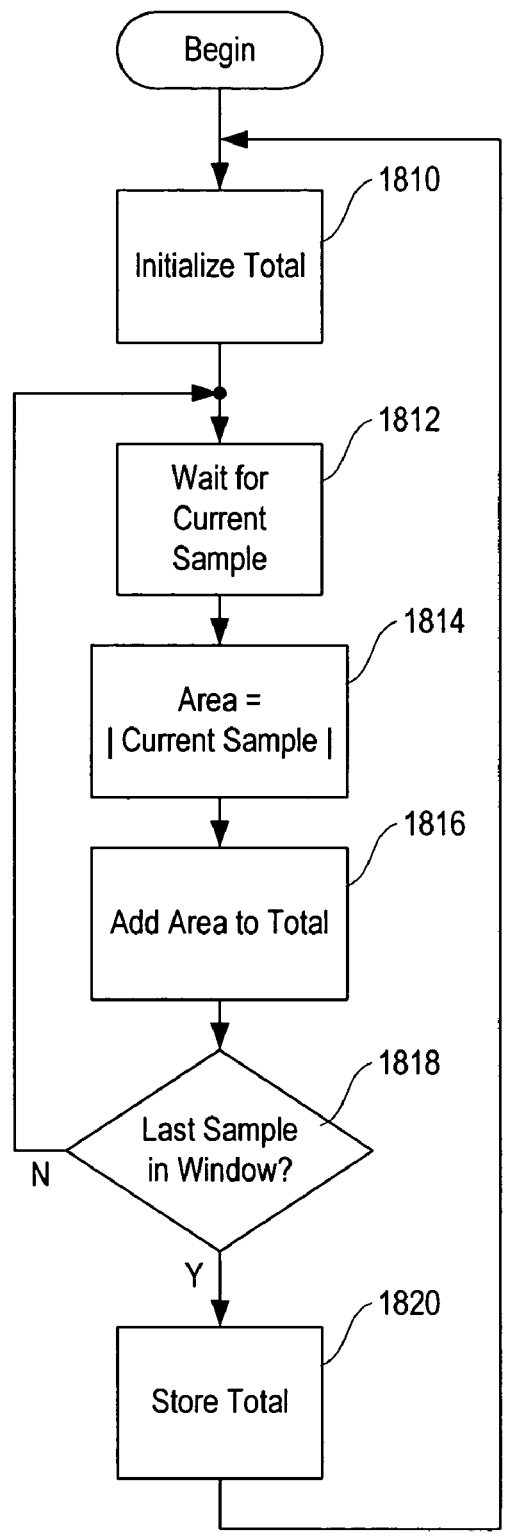
FIG. 18 is a flow chart illustrating the process performed by hardware functional components of the waveform analyzer of FIG. 7 in calculating the area function as illustrated in FIG. 17.

The areas under the curve illustrated in FIG. 17 are calculated as shown by the flow chart of FIG. 18, which is invoked at the beginning of a time window. Initially, an area total variable is initialized to zero (step 1810). The current sample is awaited (step 1812), and the absolute value of the current sample is measured (step 1814).

As with the line length calculation method described above (with reference to FIG. 15), in various alternative embodiments of the invention, the current sample (as measured in step 1814, described above) may be mathematically transformed in useful nonlinear ways. For example, it may be advantageous in certain circumstances to calculate the square of the current sample rather than its absolute value. The result of such a transformation by squaring each sample will generally be more representative of signal energy, though it is contemplated that other transformations (such as square root, exponentiation, logarithm, and other nonlinear functions) might also be advantageous in certain circumstances. Whether or not to perform such a transformation and the nature of any transformation to be performed are preferably programmable parameters of the device 110.

The calculated absolute value is added to the total (step 1816). If there are more samples remaining in the window 1712 (step 1818), another current sample is awaited (step 1812) and the process continues. Otherwise, the area calculation for the window 1712 is complete, and the total is stored (step 1820), the total is re-initialized to zero (step 1810), and the process continues.

As with the half wave and line length analysis methods set forth above, the area calculation does not need to terminate; it can be free-running yet interruptible. If the area calculation is restarted after having been suspended, it should be re-initialized and restarted at the beginning of a window. This synchronization can be accomplished through hardware interrupts.

Figure 19:
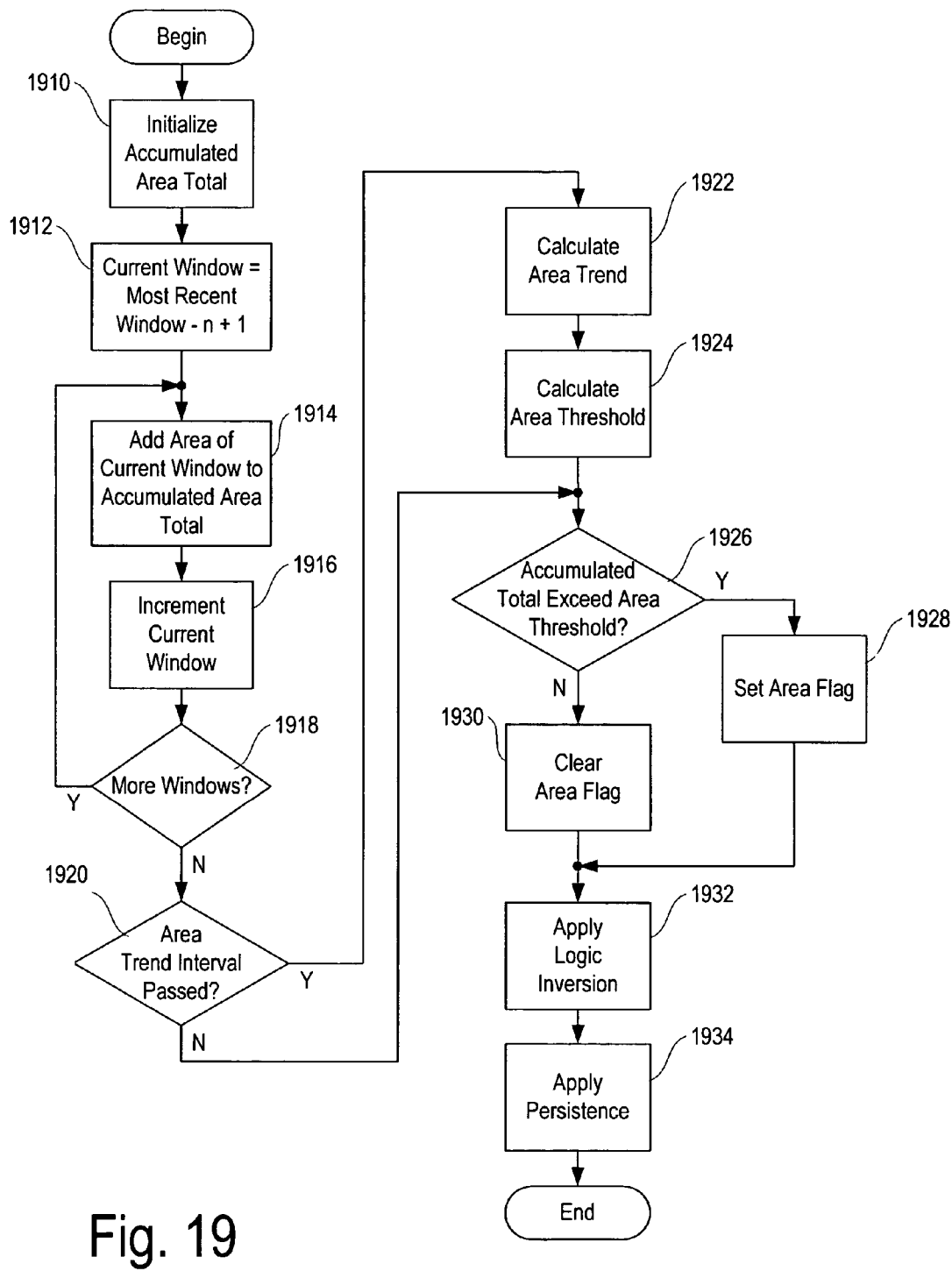
FIG. 19 is a flow chart illustrating the process performed by software in the central processing unit in calculating and analyzing the area function of an EEG signal.

The line lengths calculated as shown in FIG. 18 are then processed as indicated in the flow chart of FIG. 19, which is performed after each window 1712 is calculated and stored (step 1820).

The process begins by calculating a running accumulated area total over a period of n time windows. Where n>1, the effect is that of a sliding window; in an alternative embodiment an actual sliding window processing methodology may be used. First, the accumulated total is initialized to zero (step 1910). A current window pointer is set to indicate the $n^{th}$-last window, i.e., the window (n−1) windows before the most recent window (step 1912). The area for the current window is added to the total (step 1914), the current window pointer is incremented (step 1916), and if there are more windows between the current window and the most recent (last) window (step 1918), the adding and incrementing steps (1914-1916) are repeated. Accordingly, by this process, the resulting total includes the areas under the curve for each of the n most recent windows.

In the disclosed embodiment of the invention, the accumulated total area is compared to a dynamic threshold, which is based on a trend of recently observed areas. The trend is recalculated regularly and periodically, after each recurring area trend interval (which is preferably a fixed or programmed time interval). Each time the area trend interval passes (step 1920), the area trend is calculated or updated (step 1922). In a presently preferred embodiment of the invention, this is accomplished by calculating a normalized moving average of several trend samples, each of which represents several consecutive windows of areas. A new trend sample is taken and the moving average is recalculated upon every area trend interval. The number of trend samples used in the normalized moving average and the number of consecutive windows of area measurements per trend sample are preferably both fixed or programmable values.

After the area trend has been calculated, the area threshold is calculated (step 1924) based on the new area trend. As with line length, discussed above, the threshold may be set as either a percentage of the area trend (either below 100% for a threshold that is lower than the trend, or above 100% for a threshold that is higher than the trend) or alternatively a fixed numeric offset from the area trend (either negative for a threshold that is lower than the trend, or positive for a threshold that is higher than the trend).

The first time the process of FIG. 19 is performed, there is generally no area trend against which to set a threshold. Accordingly, for the first several passes through the process (until a sufficient amount of EEG data has been processed to establish a trend), the threshold is essentially undefined and the area detector should not return a positive detection. Some "settling time" is required to establish trends and thresholds before a detection can be made.

If the accumulated total exceeds the calculated threshold (step 1926), then a flag is set (step 1928) indicating an area-based event detection on the current window analysis unit channel 714. Otherwise, the flag is cleared (step 1930). Once the area flag has been either set or cleared, logic inversion is applied (step 1932), persistence is applied (step 1934), and the procedure terminates.

The resulting persistent area flag indicates whether the threshold has been exceeded within one or more windows over a time period corresponding to the area flag persistence. As will be discussed in further detail below, area event detections can be combined with the half wave event detections, line length event detections, as well as any other applicable detection criteria according to the invention.

In a preferred embodiment of the invention, each threshold for each channel and each analysis tool can be programmed separately; accordingly, a large number of individual thresholds may be used in a system according to the invention. It should be noted thresholds can vary widely; they can be updated by a physician via the external programmer 312 (FIG. 3), and some analysis tool thresholds (e.g., line length and area) can also be automatically varied depending on observed trends in the data. This is preferably accomplished based on a moving average of a specified number of window observations of line length or area, adjusted as desired via a fixed offset or percentage offset, and may compensate to some extent for diurnal and other normal variations in brain electrophysiological parameters.

With regard to the flow charts of FIGS. 11-13, 15-16, and 18-19, it should be noted that there can be a variety of ways these processes are implemented. For example, state machines, software, hardware (including ASICs, FPGAs, and other custom electronics), and various combinations of software and hardware, are all solutions that would be possible to practitioners of ordinary skill in the art of electronics and systems design. It should further be noted that the steps performed in software need not be, as some of them can be implemented in hardware, if desired, to further reduce computational load on the processor. In the context of the invention, it is not believed to be advantageous to have the software perform additional steps, as that would likely increase power consumption.

In an embodiment of the invention, one of the detection schemes set forth above (e.g., half wave detection) is adapted to use an X of Y criterion to weed out spurious detections. This can be implemented via a shift register, as usual, or by more efficient computational methods. As described above, half waves are analyzed on a window-by-window basis, and as described above (in connection with FIG. 13), the window results are updated on a separate analysis window interval. If the detection criterion (i.e., a certain number of half waves in less than a specified time period) is met for any of the half waves occurring in the most recent window, then detection is satisfied within that window. If that occurs for at least X of the Y most recent windows, then the half wave analysis tool triggers a detection. If desired, other detection algorithms (such as line length and area) may operate in much the same way: if thresholds are exceeded in at least X of the Y most recent windows, then the corresponding analysis tool triggers a detection.

Also, in the disclosed embodiment, each detection flag, after being set, remains set for a selected amount of time, allowing them to be combined by Boolean logic (as described below) without necessarily being simultaneous.

Figure 20:
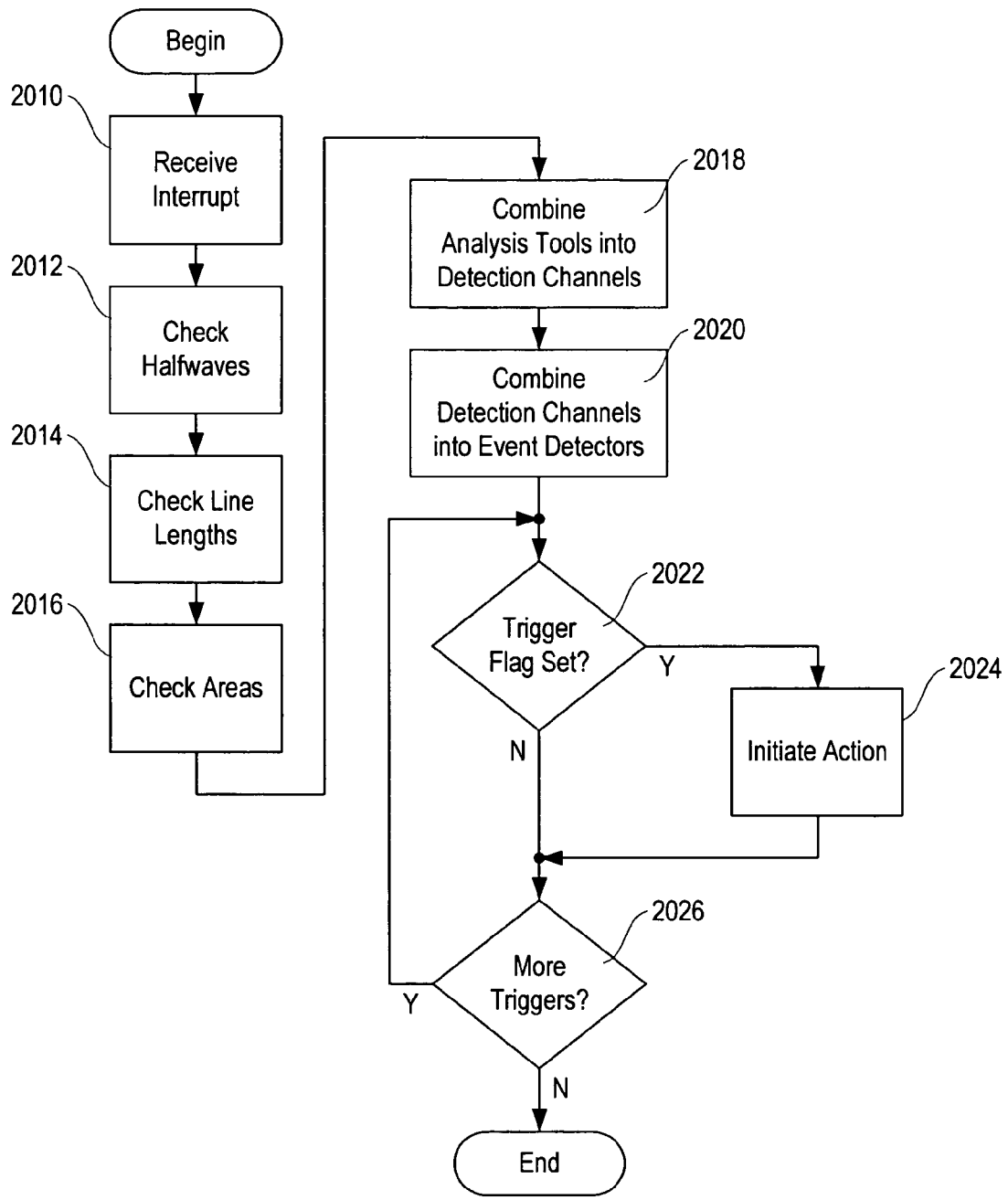
FIG. 20 is a flow chart illustrating the process performed by event-driven software in the central processing unit to analyze half wave, line length, and area information for detection according to the invention.

As indicated above, each of the software processes set forth above (FIGS. 12-13, 16, and 19) correspond to functions performed by the wave morphology analysis units 712 and window analysis units 714. Each one is initiated periodically, typically once per detection window (1212, 1512). The outputs from the half wave and window analysis units 712 and 714, namely the flags generated in response to counted qualified half waves, accumulated line lengths, and accumulated areas are combined to identify event detections as functionally illustrated in FIG. 8 and as described via flow chart in FIG. 20.

The process begins with the receipt of a timer interrupt (step 2010), which is typically generated on a regular periodic basis to indicate the edges of successive time windows. Accordingly, in a system or method according to the disclosed embodiment of the invention, such a timer interrupt is received every 128 ms, or as otherwise programmed or designed. Then the half wave (step 2012, FIGS. 12-13), line length (step 2014, FIG. 16), and area (step 2016, FIG. 19) analysis tools are evaluated with respect to the latest data generated thereby, via the half wave analysis flag, the line length flag, and the area flag for each active channel. The steps of checking the analysis tools (steps 2012, 2014, and 2016) can be performed in any desired order or in parallel, as they are generally not interdependent. It should be noted that the foregoing analysis tools should be checked for every active channel, and may be skipped for inactive detection channels.

Flags, indicating whether particular signal characteristics have been identified in each active channel, for each active analysis tools, are then combined into detection channels (step 2018) as illustrated in FIG. 8. In the disclosed embodiment of the invention, this operation is performed as described in detail below with reference to FIG. 21. Each detection channel is a Boolean AND combination of analysis tool flags for a single channel, and as disclosed above, there are preferably at least eight channels in a system according to the invention.

The flags for multiple detection channels are then combined into event detector flags (step 2020), which are indicative of identified neurological events calling for action by the device. This process is described below, see FIG. 20, and is in general a Boolean combination of detection channels, if there is more than one channel per event detector.

If an event detector flag is set (step 2022), then a corresponding action is initiated (step 2024) by the device. Actions according to the invention can include the presentation of a warning to the patient, an application of therapeutic electrical stimulation, a delivery of a dose of a drug, an initiation of a device mode change, or a recording of certain EEG signals; it will be appreciated that there are numerous other possibilities. It is preferred, but not necessary, for actions initiated by a device according to the invention to be performed in parallel with the sensing and detection operations described in detail herein. It should be recognized that the application of electrical stimulation to the brain may require suspension of certain of the sensing and detection operations, as electrical stimulation signals may otherwise feed back into the detection system 422 (FIG. 4), causing undesirable results and signal artifacts.

Multiple event detector flags are possible, each one representing a different combination of detection channel flags. If there are further event detector flags to consider (step 2026), those event detector flags are also evaluated (step 2022) and may cause further actions by the device (step 2024). It should be noted that, in general, actions performed by the device (as in step 2024) may be in part dependent on a device state—even if certain combinations of events do occur, no action may be taken if the device is in an inactive state, for example.

Figure 21:
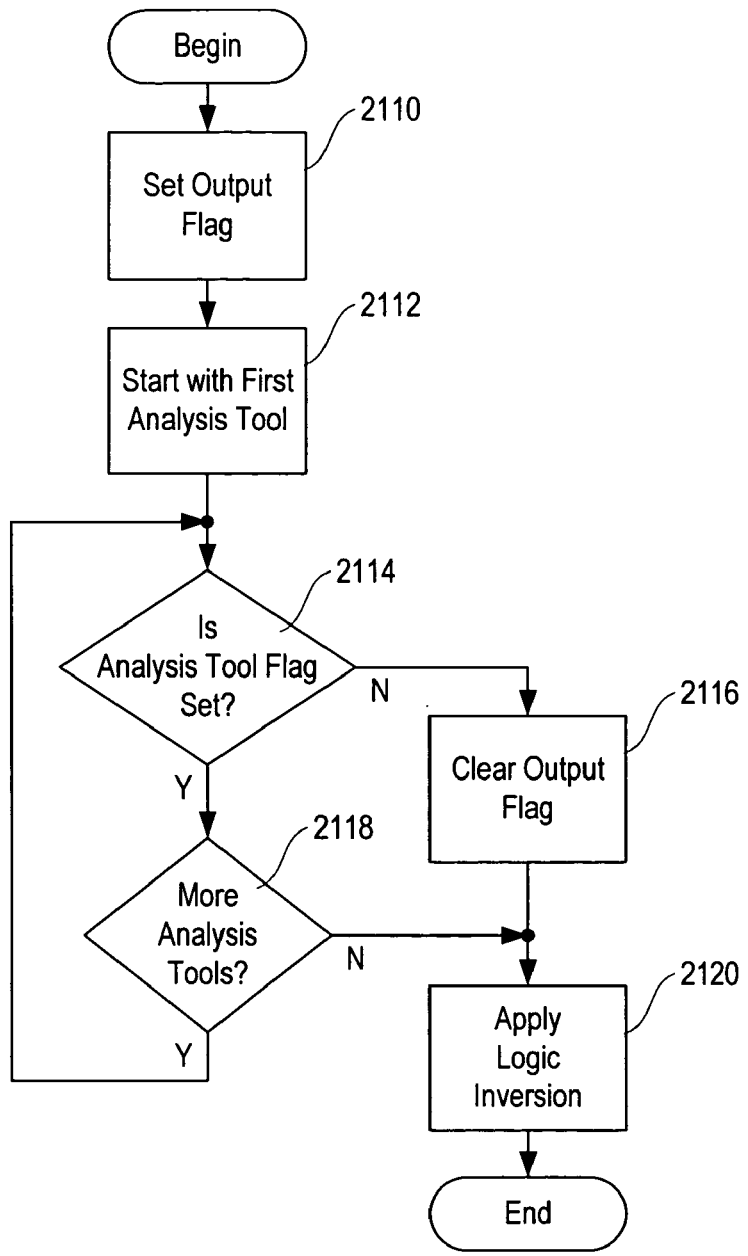
FIG. 21 is a flow chart illustrating the combination of analysis tools into detection channels in an embodiment of the invention.

As described above, and as illustrated in FIG. 20 as step 2018, a corresponding set of analysis tool flags is combined into a detection channel flag as shown in FIG. 21 (see also FIG. 8). Initially the output detection channel flag is set (step 2110). Beginning with the first analysis tool for a particular detection channel (step 2112), if the corresponding analysis tool flag is not set (step 2114), then the output detection channel flag is cleared (step 2116).

If the corresponding analysis tool flag is set (step 2114), the output detection channel flag remains set, and further analysis tools for the same channel, if any (step 2118), are evaluated. Accordingly, this combination procedure operates as a Boolean AND operation—if any of the enabled and active analysis tools for a particular detection channel does not have a set output flag, then no detection channel flag is output by the procedure.

A clear analysis tool flag indicates that no detection has been made within the flag persistence period, and for those analysis tools that employ an X of Y criterion, that such criterion has not been met. In certain circumstances, it may be advantageous to also provide detection channel flags with logic inversion. Where a desired criterion (i.e., combination of analysis tools) is not met, the output flag is set (rather than cleared, which is the default action). This can be accomplished by providing selectable Boolean logic inversion (step 2120) corresponding to each event detector.

Figure 22:
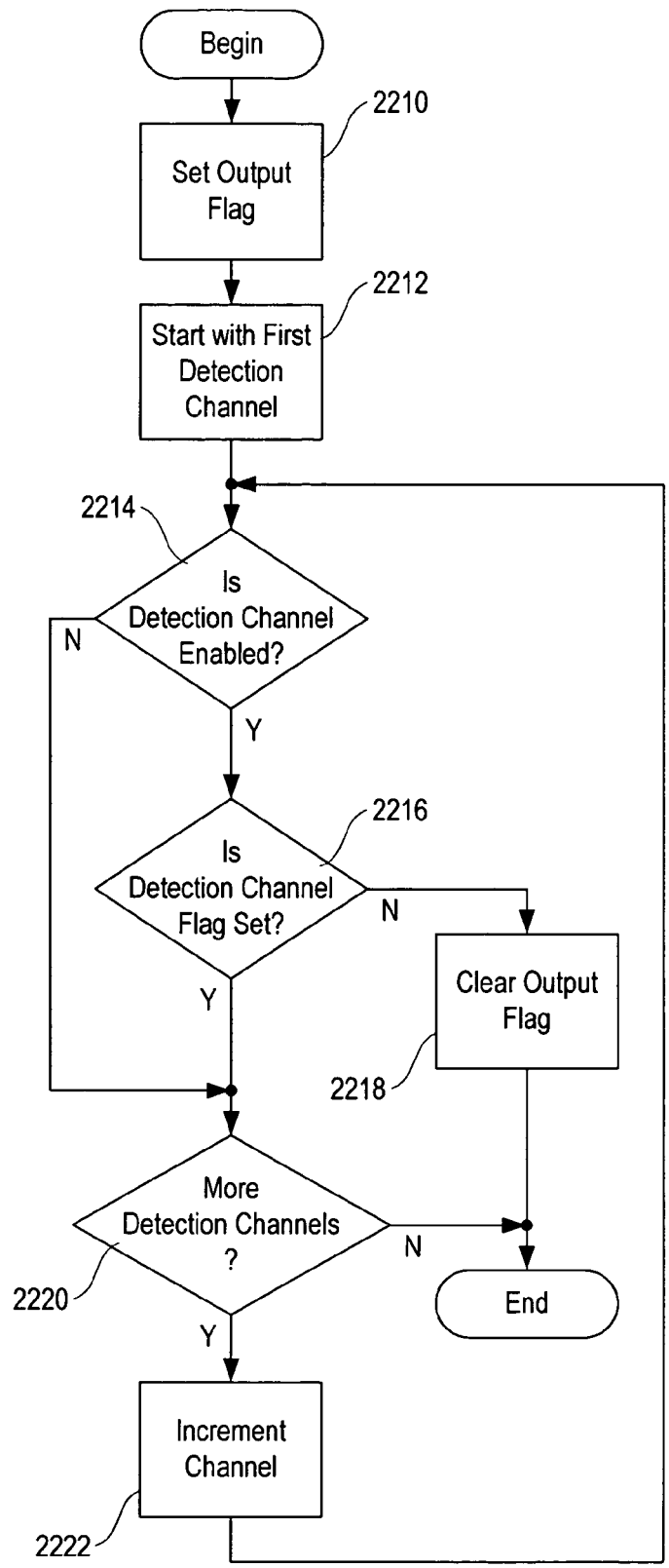
FIG. 22 is a flow chart illustrating the combination of detection channels into event detectors in an embodiment of the invention.

Also as described above, and as illustrated in FIG. 20 as step 2020, multiple detection channel flags are combined into a single event detector flag as shown in FIG. 22 (see also FIG. 8). Initially the output event detector flag is set (step 2210). Beginning with the first detection channel for a particular event detector (step 2212), if the channel is not enabled (step 2214), then no check is made. If the channel is enabled and the corresponding detection channel flag is not set (step 2216), then the output event detector flag is cleared (step 2218) and the combination procedure exits. If the corresponding detection channel flag is set (step 2216), the output event detector flag remains set, and further detection channels, if any (step 2220), are evaluated after incrementing the channel being considered (step 2222). Accordingly, this combination procedure also operates as a Boolean AND operation—if any of the enabled and active detection channels does not have a set output flag, then no event detector flag is output by the procedure. It should also be observed that a Boolean OR combination of detection channels may provide useful information in certain circumstances; a software or hardware flow chart accomplishing such a combination is not illustrated, but could easily be created by an individual of ordinary skill in digital electronic design or computer programming.

An implantable version of a system according to the invention advantageously has a long-term average current consumption on the order of 10 microamps, allowing the implanted device to operate on power provided by a coin cell or similarly small battery for a period of years without need for replacement. It should be noted, however, that as battery and power supply configurations vary, the long-term average current consumption of a device according to the invention may also vary and still provide satisfactory performance.

It should be observed that while the foregoing detailed description of various embodiments of the present invention is set forth in some detail, the invention is not limited to those details and an implantable neurostimulator or neurological disorder detection device made according to the invention can differ from the disclosed embodiments in numerous ways. In particular, it will be appreciated that embodiments of the present invention may be employed in many different applications to detect anomalous neurological characteristics in at least one portion of a patient's brain. It will be appreciated that the functions disclosed herein as being performed by hardware and software, respectively, may be performed differently in an alternative embodiment. It should be further noted that functional distinctions are made above for purposes of explanation and clarity; structural distinctions in a system or method according to the invention may not be drawn along the same boundaries. Hence, the appropriate scope hereof is deemed to be in accordance with the claims as set forth below.

What is claimed is:

1. An implantable device for detecting a neurological event by analyzing an electrical signal from a patient's brain, the device comprising:
   an implantable control module;
   a central processing unit located within the control module; and
   a detection subsystem located within the control module and comprising a waveform analyzer having a window-based analyzer configured to identify waveform features using sample-to-sample amplitude variations of the electrical signal during a window and a feature-based analyzer configured to identify half wave features of the electrical signal.

2. The implantable device of claim 1, wherein the detection subsystem performs a first portion of an event detection procedure, and the central processing unit performs a second portion of the event detection procedure.

3. The implantable device of claim 1, wherein the central processing unit and the detection subsystem are enclosed within a housing, and wherein the housing is adapted to be implanted in the patient.

4. The implantable device of claim 3, wherein the housing is adapted to be implanted intracranially in the patient.

5. The implantable device of claim 1, wherein the neurological event comprises an epileptic seizure, an onset of an epileptic seizure, a precursor to an epileptic seizure, an episode of a movement disorder, an onset of an episode of a movement disorder, a precursor to an episode of a movement disorder, a migraine headache, an onset of a migraine headache, a precursor to a migraine headache, an episode of pain, an onset of an episode of pain, a precursor to an episode of pain, an episode of depression, an onset of an episode of depression, or a precursor to an episode of depression.

6. The implantable device of claim 1, wherein the neurological event comprises an event predictive of an episode of clinical symptoms selected from the group consisting of an epileptic seizure, an episode of a movement disorder, a migraine headache, an episode of pain, and an episode of depression.

7. The implantable device of claim 1, wherein the detection subsystem comprises at least one electronics module.

8. The implantable device of claim 1, wherein the feature-based analyzer comprises a wave morphology analyzer.

9. An implantable device for detecting a neurological event by analyzing an electrical signal from a patient's brain, the device comprising:
   an implantable control module;
   a detection subsystem located within the control module and adapted to identify at least one half wave feature in the electrical signal and calculate at least one window parameter in the electrical signal using sample-to-sample amplitude variations of the electrical signal during a window; and
   a central processing unit located within the control module and adapted to analyze the at least one feature and the at least one window parameter, and to initiate an action in accordance therewith.

10. The implantable device of claim 1, wherein the detection subsystem is configured to receive the electrical signal from an electrode pair, identify at least one feature in the electrical signal, calculate at least one window parameter in the electrical signal; provide an indication to the implantable device to perform an action in accordance with an indication from the detection subsystem, and sample the electrical signal to create a sampled digital signal,
   wherein the feature-based analyzer is configured to identify a half wave feature in the sampled digital signal includes the feature-based analyzer is configured to locate a half wave in the sampled digital signal, determine whether an amplitude of the half wave exceeds an amplitude threshold and whether a duration of the half wave exceeds a duration threshold, and if both thresholds are met, label the half wave as a qualified half wave, and if the half wave is a qualified half wave, store a record representative of the qualified half wave, and
   wherein the window analyzer is configured to calculate a window parameter in the sampled digital signal.

11. The implantable device of claim 10, wherein the feature-based analyzer is configured to locate a half wave in the sampled digital signal includes:
   the feature-based analyzer is configured to find a starting point for the half wave, wherein the starting point has a first sample value equal to an initial current EEG sample value;
   the feature-based analyzer is configured to calculate an ending threshold by combining the current EEG sample value and a hysteresis value;
   the feature-based analyzer is configured to measure a current EEG sample value;
   the feature-based analyzer is configured to compare the current EEG sample value to the ending threshold;
   the feature-based analyzer is configured to repeat the calculate, measure, and compares until the current EEG sample value exceeds the ending threshold;
   the feature-based analyzer is configured to establish an ending point for the half wave, wherein the ending point has an ending sample value equal to the current EEG sample value;
   the feature-based analyzer is configured to calculate a half wave amplitude equal to a difference between the first sample value and the current EEG sample value; and
   the feature-based analyzer is configured to calculate a half wave duration equal to a difference between a time corresponding to the ending point and a time corresponding to the starting point.

12. A method for detecting a neurological event by analyzing an electrical signal from a patient's brain with an implantable device, the method comprising:
   receiving the electrical signal with an electrode pair;
   processing the electrical signal with a detection subsystem, wherein the detection subsystem is adapted to identify at least one half wave feature in the electrical signal and calculate at least one window parameter in the electrical signal using sample-to-sample amplitude variations of the electrical signal during a window; and
   causing the implantable device to perform an action in accordance with an indication from the detection subsystem.

13. The method for detecting a neurological event of claim 12, wherein the processing step comprises:
   sampling the electrical signal to create a sampled digital signal;
   identifying a feature in the sampled digital signal with a wave morphology analyzer; and
   calculating a window parameter in the sampled digital signal with a window analyzer.

14. The method for detecting a neurological event of claim 13, wherein the causing step comprises:
   processing the feature and the window parameter to determine whether to set a detection flag;
   if the detection flag is set, performing an action in accordance with the detection flag.

15. A method for detecting a neurological event by analyzing an electrical signal from a patient's brain with an implantable device, the method comprising:
   receiving the electrical signal with an electrode pair;
   processing the electrical signal with a detection subsystem, wherein the detection subsystem is adapted to identify at least one half wave feature in the electrical signal and calculate at least one window parameter in the electrical signal; and
   causing the implantable device to perform an action in accordance with an indication from the detection subsystem,
   wherein the processing the electrical signal comprises:
      sampling the electrical signal to create a sampled digital signal;
      identifying a feature in the sampled digital signal with a wave morphology analyzer; and
      calculating a window parameter in the sampled digital signal with a window analyzer,
   wherein calculating a window parameter comprises computing a line length function.

16. A method for detecting a neurological event by analyzing an electrical signal from a patient's brain with an implantable device, the method comprising:
   receiving the electrical signal with an electrode pair;
   processing the electrical signal;
   converting the electrical signal into a digital signal;
   performing a half wave feature extraction operation on the digital signal;
   performing a window calculation operation on the digital signal using sample-to-sample amplitude variations of the digital signal during a window;

analyzing a result from the half wave feature extraction operation;
analyzing a result from the window calculation operation; and
performing an action in accordance with the result from the half wave feature extraction operation and the result from the window calculation operation.

17. A method for detecting a neurological event by analyzing an electrical signal from a patient's brain with an implantable device, the device having a processor and a detection subsystem, the method comprising:
causing the processor to enter a low-power mode;
measuring a half wave feature characteristic of the electrical signal with the detection subsystem;
measuring a window characteristic of the electrical signal with the detection subsystem;
causing the processor to exit the low-power mode;
analyzing the half wave feature characteristic and the window characteristic with the processor; and
performing an action in accordance with the half wave feature characteristic and the window characteristic.

18. The method for detecting a neurological event of claim 17, wherein the low-power mode is characterized by relative inactivity.

19. An implantable device for detecting a neurological event by analyzing an electrical signal from a patient's brain, the device comprising:
an implantable control module;
a central processing unit located within the control module; and
a detection subsystem located within the control module and comprising a waveform analyzer having a window-based analyzer and a feature-based analyzer configured to identify half wave features of the electrical signal, wherein the detection subsystem is configured to receive the electrical signal from an electrode pair, identify at least one feature in the electrical signal, calculate at least one window parameter in the electrical signal, provide an indication to the implantable device to perform an action in accordance with an indication from the detection subsystem, and sample the electrical signal to create a sampled digital signal,
wherein the window analyzer is configured to calculate a window parameter in the sampled digital signal, wherein the window-based analyzer is adapted to analyze a line length function and an area function in the electrical signal,
wherein the feature-based analyzer is configured to identify a half wave feature in the sampled digital signal includes the feature-based analyzer is configured to locate a half wave in the sampled digital signal, determine whether an amplitude of the half wave exceeds an amplitude threshold and whether a duration of the half wave exceeds a duration threshold, and if both thresholds are met, label the half wave as a qualified half wave, and if the half wave is a qualified half wave, store a record representative of the qualified half wave, wherein the feature-based analyzer is adapted to analyze the half waves in the electrical signal.

* * * * *